United States Patent
Nachaliel et al.

(10) Patent No.: US 7,409,243 B2
(45) Date of Patent: Aug. 5, 2008

(54) BREAST CANCER DETECTION

(75) Inventors: Ehud Nachaliel, Lower-Galilee (IL); Sarah Lenington, Ringwood, NJ (US)

(73) Assignee: Mirabel Medical Ltd., Migdal HaEmek (IL)

( * ) Notice: Subject to any disclaimer, the term of this patent is extended or adjusted under 35 U.S.C. 154(b) by 231 days.

(21) Appl. No.: 10/116,690

(22) Filed: Apr. 4, 2002

(65) Prior Publication Data

US 2002/0183645 A1 Dec. 5, 2002

(30) Foreign Application Priority Data

Apr. 4, 2001 (IL) .................. 142451

(51) Int. Cl.
*A61B 5/05* (2006.01)

(52) U.S. Cl. ............................ 600/547

(58) Field of Classification Search ............ 600/382, 600/384, 386–394, 547, 442; 128/920–925
See application file for complete search history.

(56) References Cited

U.S. PATENT DOCUMENTS

| | | |
|---|---|---|
| 3,608,543 A | 9/1971 | Longini |
| 4,036,217 A | 7/1977 | Ito et al. |
| 4,291,708 A | 9/1981 | Frei et al. |
| 4,328,809 A | 5/1982 | Hirschowitz et al. |
| 4,458,694 A | 7/1984 | Sollish et al. |
| 4,539,640 A | 9/1985 | Fry et al. |
| 4,617,939 A | 10/1986 | Brown et al. |
| 4,768,516 A | 9/1988 | Stoddart et al. |
| 5,143,079 A | 9/1992 | Frei et al. |
| 5,415,164 A | 5/1995 | Faupel et al. |
| 5,660,177 A | 8/1997 | Faupel et al. |
| 5,715,821 A | 2/1998 | Faupel |
| 5,749,369 A | 5/1998 | Rabinovich et al. |
| 5,800,350 A | 9/1998 | Coppleson et al. |
| 5,810,742 A | 9/1998 | Pearlman |
| 6,122,544 A | 9/2000 | Organ |
| 6,167,300 A | 12/2000 | Cherepenin et al. |
| 6,179,786 B1 | 1/2001 | Young |
| 6,179,790 B1 | 1/2001 | Cundari et al. |
| 6,351,666 B1 * | 2/2002 | Cuzick et al. ............... 600/547 |
| 6,500,117 B1 * | 12/2002 | Hancock, Jr. ............... 600/300 |

(Continued)

FOREIGN PATENT DOCUMENTS

WO     WO 01/43630     6/2001

(Continued)

OTHER PUBLICATIONS

Piperno, G. et al.; "Breast Cancer Screening by Impedance Measurements;" Frontiers Med. Biol. Eng.; vol. 2; pp. 111-117. 1990.

(Continued)

*Primary Examiner*—Max F. Hindenburg
*Assistant Examiner*—Jonathan Foreman

(57) ABSTRACT

Apparatus for breast examination, comprising:
 a sensing unit including a probe capable of sensing electrical signals from a surface of a breast, including at least a portion of the nipple thereof;
 a processor operative to generate, based on sensed signals from only the nipple of the breast, optionally adjusted by values outside the breast, a malignancy score relating to the need of additional testing of the breast; and
 a display operative to indicate at least the range of the malignancy score.

39 Claims, 7 Drawing Sheets

U.S. PATENT DOCUMENTS

| | | |
|---|---|---|
| 6,768,921 B2 * | 7/2004 | Organ et al. ................ 600/547 |
| 2001/0051774 A1 | 12/2001 | Littrup et al. |
| 2003/0078482 A1 * | 4/2003 | Kenan et al. ................ 600/372 |
| 2003/0078510 A1 | 4/2003 | Olson et al. |

FOREIGN PATENT DOCUMENTS

| WO | WO 01/64102 | 9/2001 |
|---|---|---|

OTHER PUBLICATIONS

Piperno, G. et al.; "Breast Electriccal Impedance and Estrogen Use in Postmenopausal Women;" Maturitas: The European Menopause Journal; 41; pp. 17-22. Jan. 30, 2002.

* cited by examiner

BREAST CANCER DETECTION

FIELD OF THE INVENTION

The present invention relates to systems for tissue characterization and particularly for detecting breast cancer.

BACKGROUND OF THE INVENTION

Breast cancer is a major cause of mortality in women. One of the factors that influences the chances of curing a patient having breast cancer is early detection of the disease. The major methods for detecting breast cancer currently in use are X-ray mammography imaging and ultrasound imaging. In detecting breast cancer, an image of the breast is generated, using one of the above mentioned imaging modalities, and a physician inspects the image to determine whether the image is indicative of breast cancer. Such inspection of images requires image analysis specialization from the physician, which adds to the cost of the cancer detecting procedure and/or limits the availability of the procedure to relatively large medical centers. Therefore, in general, only women in risk groups of breast cancer undergo tests for early detection of breast cancer. These risk groups include, for example, women above the age of about 45 and women having a family history of breast cancer. The chances that a woman in a risk group has cancer is less than 10% and therefore even many women in the risk groups do not go for regular breast cancer detection procedures as recommended.

For women not in a risk group, for example in the age group of 25-45, there are very low chances, in accordance with current practice, that their cancer will be detected at an early stage. These women, however, have a chance of about 3 to 1000 to have breast cancer, which may not be detected until the cancer is in advanced stages. Women physicians and aware women perform palpation tests in search for cancer and woman who have suspected lumps detected in their breasts by palpitation are sent for further screening by ultrasound and/or mammography and/or biopsy.

The TS2000 cancer detection system available from Trans-Scan, described for example in Assenheimer M, Laver-Moskovitz O, Malonek D, Manor D, Nahaliel U, Nitzan R, Saad A, "The T-Scan™ technology: electrical impedance as a diagnostic tool for breast cancer detection", Physiology Measurements 22:1-8, 2001, the disclosure of which is incorporated herein by reference, provides in addition to an image, a malignancy score on a scale with about 100 values. This score is used by the physician in addition to the image and other indicators to aid in determining the existence of cancer.

Another method for detecting breast cancer includes injecting a liquid into the breast, sucking the injected liquid from the breast and examining the sucked liquid for cancerous particles. This method, however, is very painful and therefore cannot be used for large scale cancer examination. In addition, the results require cytology and are not provided on the spot.

U.S. Pat. No. 5,800,350, to Coppleson et al., the disclosure of which is incorporated herein by reference, describes a probe adapted to apply a plurality of stimuli to a suspected tissue. According to detected responses to the stimuli, the probe provides an indication of the surface tissue type (e.g., normal, pre-cancerous/cancerous, unknown) of the suspected tissue. The probe of U.S. Pat. No. 5,800,350 is not suitable for use with the breast, as cancerous cells in the breast are not generally on the surface of the breast.

An article titled "Breast Electrical Impedance and Estrogen Use in Postmenopausal Women", G. Piperno, S. Lenington, Mauturitas 41 (2002), the disclosure of which is incorporated herein by reference, describes a clinical test which suggests a correlation between electrical measurements on the nipple and estrogen activity in breast tissue.

Other existing methods in more limited use include infrared imaging.

SUMMARY OF THE INVENTION

An aspect of some embodiments of the present invention relates to an apparatus for breast cancer examination, which performs a non-invasive test of the breast. The apparatus provides, in an embodiment thereof, a single output responsive to the non-invasive test, which includes a malignancy score on a single dimension scale. By providing a score that does not require interpretation, the apparatus is made simple and may be utilized by a large span of medical professionals and optionally even by non-professionals. Thus, the apparatus may be used in many locations, including local clinics, and reach many patients that would not come to central cancer screening locations.

In some embodiments of the invention, the non-invasive test includes generating a multi-pixel image of a portion of the breast, with the malignancy score being generated based on an evaluation of the generated image.

Optionally, the non-invasive test includes one or more impedance measurements of breast tissue. Alternatively or additionally, the non-invasive test includes optical, thermal and/or other known cancer tests.

In some embodiments of the invention, the image is formed with the electrode or electrodes placed against the front of the breast, so that the image includes all or part of the nipple. In some embodiments of the invention, the score is generated using data only from the nipple (and optionally only from the areola) optionally normalized by data acquired from other measurements.

In some embodiments of the invention electrodes having a hole or depression formed therein with a diameter suitable for insertion of the tip of the nipple are used. Some of these embodiments utilize multi-element probes and others utilize a single electrode probe having a diameter small enough to encompass only areola or a portion thereof. In some embodiments of the invention, the electrode is a circular, square, rectangular or other shaped electrode having an area small enough so that it is only covers a portion of the areola and not the surrounding tissue or the tip of the nipple.

In some embodiments of the invention, the apparatus is set to have a relatively high false positive (indication of possible cancer to healthy patients) rate and a relatively low false negative (indication of healthy tissue to cancerous patients) rate. Optionally, the apparatus is used for a first screening procedure and patient's receiving a positive indication are referred to further tests, for example, of x-ray mammography and/or ultrasound imaging.

In some embodiments of the invention, the apparatus performs the tests substantially without incurring pain to the patient and/or without using ionizing radiation. Thus, cancer tests using the apparatus may be performed on large populations that would not have been tested with prior art apparatus, with more difficult tests being performed on a smaller population.

An aspect of some embodiments of the present invention relates to an apparatus for breast cancer examination, which performs a non-invasive test of the breast and provides a binary malignancy score (e.g., more tests required/not required) responsive to the test.

An aspect of some embodiments of the present invention relates to a method of providing a malignancy score to a breast based on impedance measurements taken from a portion of the breast including the nipple. In many cases, breast cancer develops in early stages from ducts leading to the nipple. By determining whether a breast includes abnormal impedance values in the area of the nipple (and in some embodiments, limited to the areola surrounding the tip of the nipple), it may be determined with some confidence, whether the breast includes cancerous or pre-cancerous tissue. In addition, the low impedance of the upper surface of the nipple attracts currents from throughout the breast. Therefore, signals sensed at the nipple can provide an indication on the entire breast.

An aspect of some embodiments of the invention relates to a method of providing a patient malignancy score based on measurements from both breasts of the patient. The patient malignancy score provides an indication on the probability of the patient having breast cancer without relating to which breast may have the cancer. One use of the present invention is in screening and referral to other modalities for further testing and localization of the lesion, if any. As such the indication of the breast in which the lesion is present is less important for screening.

An aspect of some embodiments of the present invention relates to methods of isolating an impedance value of a tissue portion whose impedance is of interest from impedance measurements of a body portion including at least one additional tissue portion, whose impedance is not currently of interest. For example, the method may be used to isolate an internal tissue impedance value from impedance measurements of the internal tissue along with the skin thereon. Alternatively or additionally, the tissue portions whose impedance is not of interest may be remote portions, such as the arm, hand and/or pectoral muscle in measuring breast tissue impedance. The method may be used also to isolate impedance values due to non-ideal contact between probes used to apply and/or measure electrical signals used for the impedance measurement. The internal tissue impedance is optionally used in determining whether an examined body portion includes a tumor, in locating the tumor and/or in determining whether the tumor is malignant.

In some embodiments of the invention, a plurality of surface impedance measurements, taken under different conditions, for example using stimulation signals with different frequencies, are acquired by a surface probe at a single location. The plurality of surface impedance measurements are fit into a model which formulates the expected impedance measurements as a function of the known frequency of the electrification signals, the unknown internal tissue impedance and, optionally, one or more additional unknown parameters, such as the unknown skin impedance. From the results of fitting the impedance measurements into the model, the internal tissue impedance is received.

In some embodiments of the invention, the model comprises a simple model, which has only a few unknown parameters (e.g., the internal tissue impedance and the skin impedance), which model is selected based on various simplifications. Using a simple model allows performing a very fast fit such that the results are received substantially instantaneously (e.g., within less than a second). Alternatively, the model depends on a plurality of additional unknown parameters (e.g., a matrix of internal tissue impedance parameters for different regions and/or a matrix of surface impedance parameters for different regions), such that the model is more accurate and requires fewer simplifications. Using a model with more unknowns, however, requires a larger number of impedance measurements and a more processing power intensive fitting procedure. Optionally, depending on the number of unknowns, a linear or non-linear optimization procedure is selected for performing the fitting into the model.

In some embodiments of the invention, the fitting into the model includes a first procedure in which the impedance of the skin is determined based on at least one of the impedance measurements and a second procedure in which the impedance of the internal tissue is determined based on at least one of the measurements and the skin impedance determined in the first procedure. The one or more surface measurements used to extract the internal tissue impedance portion may include none, some or all of the measurements used to generate the estimate of the skin impedance. In some embodiments of the invention, an imaginary part of the surface impedance measurements is used to determine the skin impedance. Thereafter, a real part of the surface impedance measurements, together with the determined skin impedance, are used to determine the internal tissue impedance.

Alternatively, the fitting is performed in a single procedure, in which the skin impedance is determined together with the internal tissue impedance using a larger set of equations, or in more than two separate procedures.

In some embodiments of the invention, the surface probe comprises a multi-element probe that generates a surface map of the impedance for each frequency. In other embodiments of the invention, the impedance probe comprises a sharp single element probe. When a sharp probe is used, the majority of the applied voltage falls across a near vicinity of the tip of the probe, thus substantially confining the measurement to a small region near the tip. This is due to the fact that the voltage falls with the square of the radius of the tip. In addition, the use of a single element sharp probe is advantageous since its electrical field model is relatively simple and therefore simplifications performed in order to reach a simple model have relatively small effects on the accuracy of the calculations.

In some embodiments of the invention, the internal tissue impedance is used to produce an indication as to whether a body portion includes malignant tissue and/or in analyzing a tumor to provide an indication as to whether the tumor is malignant. Generally, malignant tissue has a lower impedance than normal tissue. In some embodiments of the invention, the internal tissue impedance is used together with other measured parameters in determining whether a subject has a malignant tumor. The other measured parameters optionally include the impedance images generated by the surface probe and/or other impedance imaging results. Alternatively or additionally, the other measured parameters comprise measurements from other modalities, such as x-ray imaging, ultrasound imaging and/or physical examinations.

In some embodiments of the invention, a surface probe is passed over a plurality of points on a body portion. At each point, the internal tissue impedance beneath the probe is measured, as described hereinabove, so as to generate a map of the tissue impedance of the body portion.

An aspect of some embodiments of the present invention relates to a tissue descriptor, which is used to indicate healthy and malignant tissue. The tissue descriptor comprises an indicator frequency at which the imaginary admittance in an impedance imaging procedure reaches a local maximum. The indicator frequency is generally substantially higher for malignant tissue than for healthy tissue. In some embodiments of the invention, the phase of the voltage at the indicator frequency is used in determining the tissue score alone or in conjunction with other descriptors.

An aspect of some embodiments of the present invention relates to determining information on the tissue structure beneath the probe, from cupping effects on surface impedance images. Optionally, the determined information includes the impedance of the skin and/or the ratio between the impedance of the skin and the impedance of internal tissue beneath the skin. Generally, the extent of the cupping effect increases as the impedance of the skin decreases. In some embodiments of the invention, the cupping effect of a measured impedance image is determined from the image and is compared to predetermined information which correlates cupping forms with respective values of skin impedance. This can be used to determine a score directly from the cupping information.

In some embodiments of the invention, the measurements are performed in a manner which increases the cupping effect, e.g., using frequencies with a large cupping effect. Alternatively or additionally, the measurements are performed over a body region having a large cupping effect, such as the nipple of the breast. In some embodiments of the invention, the size of the cupping effect is used to indicate the presence of cancer. In some embodiments it is at least partially neutralized.

An aspect of some embodiments of the invention is related to the structure and use of electrodes used in electrostatic imaging and/or malignancy score determination. In an embodiment of the invention, electrodes having a hole or depression formed therein with a diameter suitable for insertion of the tip of the nipple are used. Some of these embodiments utilize multi-element probes and others utilize a single electrode probe having a diameter small enough to encompass only areola or a portion thereof In some embodiments of the invention, the electrode is a circular, square, rectangular or other shaped electrode having an area small enough so that it is only covers a portion of the areola and not the surrounding tissue or the tip of the nipple.

There is thus provided, in accordance with an embodiment of the invention, apparatus for breast examination, comprising:

a sensing unit including a probe capable of sensing electrical signals from a surface of a breast, including at least a portion of the nipple thereof;

a processor operative to generate, based on sensed signals from only the nipple of the breast, optionally adjusted by values outside the breast, a malignancy score relating to the need of additional testing of the breast; and a display operative to indicate at least the range of the malignancy score.

Optionally, the processor is operative to determine the malignancy score as a function of an electrical parameter of the breast. Optionally, the electrical parameter comprises an electrical parameter determined directly from the sensed signals. Optionally, the electrical parameter comprises an electrical parameter of inner tissue of the breast. Optionally, the processor is adapted to determine the malignancy score as a binary function of the electrical parameter of the breast.

Optionally, the malignancy score comprises a binary malignancy score.

In an embodiment of the invention, the processor is adapted to generate an impedance based image of the breast and the malignancy score is determined from a nipple portion of the image.

Optionally, the malignancy score is operative to indicate a need for additional tests on the average for more than twice or optionally more than 10 times the percentage in the population of malignant breasts. Optionally, the malignancy score is adapted to indicate a need for additional tests on the average for about 5% or more of the examined patients.

Optionally, the probe comprises a multi-element probe operative to produce an image of the breast, including the nipple and the processor is operative to delineate areas of the nipple and areas outside the nipple.

Optionally, the electrode comprises a hole or depression suitable for fitting the tip of the nipple therein.

Optionally, an outer periphery of the probe is within an outer edge of the nipple.

Optionally, the outer periphery of the probe is within 1 cm or 1.5 cm of the center of the hole or depression.

Optionally, the apparatus includes a plurality of different probes, adapted for matching different sized nipples.

Optionally, the probe comprises an outer guard ring and an inner sensing electrode.

Optionally, the probe comprises a single sensing electrode having an outer dimension of less than 1 cm.

Optionally, the probe comprises a multi-element probe.

Optionally, the probe comprises a marking of a position to be placed on the nipple.

Optionally, the sensor comprises at least one sensing element adapted to be placed on a surface of the body other than the breast. Optionally, the processor utilizes signals from said sensing element to adjust the values of said signals from the breast portion utilized in determining said score.

There is further provided, in accordance with an embodiment of the invention, apparatus for breast examination, comprising:

a sensing unit capable of sensing electrical signals from a breast, including at least a portion of the nipple thereof;

a processor adapted to determine the extent of said nipple portion and to generate, responsive to sensed signals from the determined portion, a malignancy score relating to the need of additional testing of the breast; and a human output interface adapted to provide the malignancy score to a user.

In an embodiment of the invention, the sensing unit comprises a surface probe, optionally a multi-element probe. Optionally, the surface probe comprises a marking of a position to be placed on the nipple. Optionally, the surface probe comprises a hole or depression adapted to receive the nipple.

Optionally, the surface probe comprises at least one sensing element adapted to be placed on a surface remote from the breast. Optionally, the processor utilizes signals from said sensing element to adjust the values of said signals from the breast portion utilized in determining said score.

Optionally, the score is a binary score.

There is further provided, in accordance with an embodiment of the invention, a method of determining internal tissue impedance of a body portion of a subject, through a skin layer having a surface impedance, comprising:

applying, to the subject, one or more electrical stimulus signals;

measuring a group of one or more electrical signals responsive to each of the one or more applied stimulus signals, by a surface probe placed on a surface of the body portion, said measured signals being affected by the tissue and surface impedance; and determining an impedance of the internal tissue in which the effects of the surface impedance on the measured electrical signals are at least partially neutralized, from at least one of the measured signals.

In an embodiment of the invention, determining the impedance of the internal tissue comprises estimating an impedance of the skin layer responsive to a value of at least one of the measured signals, and determining the impedance of the internal tissue, responsive to the estimated surface impedance and at least one of the measured signals. Optionally, estimating the surface impedance comprises estimating based on a comparison of an imaginary portion of an admittance determined from the measured signals of at least one of the applied signals, to a model thereof. Optionally, estimating the surface impedance comprises estimating based on a comparison of an imaginary portion of an admittance determined from the measured signals of at least two of the applied signals, to a model thereof. Optionally, determining the impedance of the internal tissue comprises determining based on a comparison of a real portion of an admittance determined from the measured signals of at least one of the applied signals, to a model thereof. Optionally, determining the impedance of the internal tissue comprises determining based on measured signals of different applied signals than those used in estimating the impedance of the surface.

In an embodiment of the invention, applying the one or more stimulus signals comprises applying a plurality of signals with different frequencies. Optionally, estimating the surface impedance comprises estimating responsive to measured signals from a plurality of groups generated responsive to stimulus signals with different frequencies.

Optionally, applying the one or more stimulus signals comprises sequentially applying a plurality of signals while the probe is urged against the breast with different pressure levels.

Optionally, applying the one or more stimulus signals comprises applying a plurality of signals from different positions.

In an embodiment of the invention, estimating the surface impedance comprises estimating responsive to a cupping effect of a map, formed of a plurality of measured signals of one of the groups of measured signals.

In an embodiment of the invention, determining the impedance of the internal tissue comprises solving a set of equations to simultaneously determine the internal tissue impedance and the surface impedance.

Optionally, applying the one or more electrical stimulus signals comprises applying signals with frequencies of up to 5000 Hz.

Optionally, the surface probe comprises a two-dimensional array of sensing elements.

Optionally, the surface probe comprises a rectangular sensing surface. Optionally, the surface probe comprises a circular sensing surface.

Optionally, measuring the group of one or more electrical signals comprises measuring while substantially all the elements of the surface probe are held at an equipotential.

Optionally, measuring the group of one or more electrical signals comprises measuring at any specific time from fewer than all the elements of the surface probe while the remaining elements of the surface probe are held floating.

In an embodiment of the invention, the surface probe comprises a single element probe.

In an embodiment of the invention, measuring the signals comprises determining measured impedance values and determining the impedance of the internal tissue comprises fitting at least some of the measured impedance values into a model of the measured impedance which is a function of the surface impedance and the internal tissue impedance. Optionally, fitting at least some of the measured values into the model comprises fitting into a model which depends on the real and imaginary impedance of the skin layer. Optionally, the model depends only on the frequency of the applied signals, the real and imaginary impedance of the skin layer and the true internal tissue impedance. Optionally, the model depends on at least two parameters additional to the frequency of the applied signals, the real and imaginary impedance of the skin layer and the real internal tissue impedance.

Optionally, the method includes passing the values of at least one of the acquired groups of signals through a low pass spatial filter.

In an embodiment of the invention, determining the impedance comprises determining a ratio between an impedance of a skin layer on the body portion and an inner tissue layer of the body portion.

Optionally, determining the impedance comprises comparing the image to a plurality of library images having respective impedance image values.

Optionally, the method includes providing a score indicative of the probability of cancer. Optionally, the score is a binary score.

There is further provided, in accordance with an embodiment of the invention, a method of determining an indicator of a body tissue, comprising:

sensing impedance measurements by a surface probe responsive to stimulus signals at a plurality of different frequencies; and estimating an indicator frequency at which one of the imaginary admittance component and the real admittance component of the impedance measurements has a local maximum, based on said sensed measurements.

In an embodiment of the invention, estimating the indicator frequency comprises fitting a plurality of the impedance measurements into a parabolic model and estimating responsive to a coefficient of the parabola.

In an embodiment of the invention, the method includes providing a malignant indication if the indicator frequency is greater than a predetermined threshold.

There is further provided, in accordance with an embodiment of the invention, a method of impedance imaging of a body portion of a subject, comprising:

applying, to the subject, one or more electrical stimulus signals;

generating a multi-element impedance image of the body portion responsive to each of the one or more applied stimulus signals, by a surface probe placed on a surface of the body portion; and determining at least one characteristic of a cupping effect of the multi-element impedance image.

Optionally, the method includes providing an indication of malignancy responsive to the at least one characteristic of the cupping effect.

There is further provided, in accordance with an embodiment of the invention, an impedance probe adapted for measuring impedance of in vivo human tissue, comprising an electrode having a depression or hole in the center thereof such that a surface of the electrode is in the form of an annulus.

Optionally, the annulus has an outer diameter of less than 2, between 2 and 2.5 or between 2.5 and 3 cm.

There is further provided, in accordance with an embodiment of the invention, an impedance probe set comprising a plurality of probes each comprising an electrode having a hole or depression therein suitable for receiving a tip of a nipple of a breast and having varying outer dimensions allowing matching of the outer dimension to a size smaller than a diameter of an areola of a nipple of a particular breast.

BRIEF DESCRIPTION OF THE DRAWINGS

Exemplary non-limiting embodiments of the invention will be described with reference to the following description of the embodiments, in conjunction with the figures. Identical structures, elements or parts which appear in more than one figure are preferably labeled with a same or similar number in all the figures in which they appear, and in which.

DETAILED DESCRIPTION OF EXEMPLARY EMBODIMENTS

Figure 1:
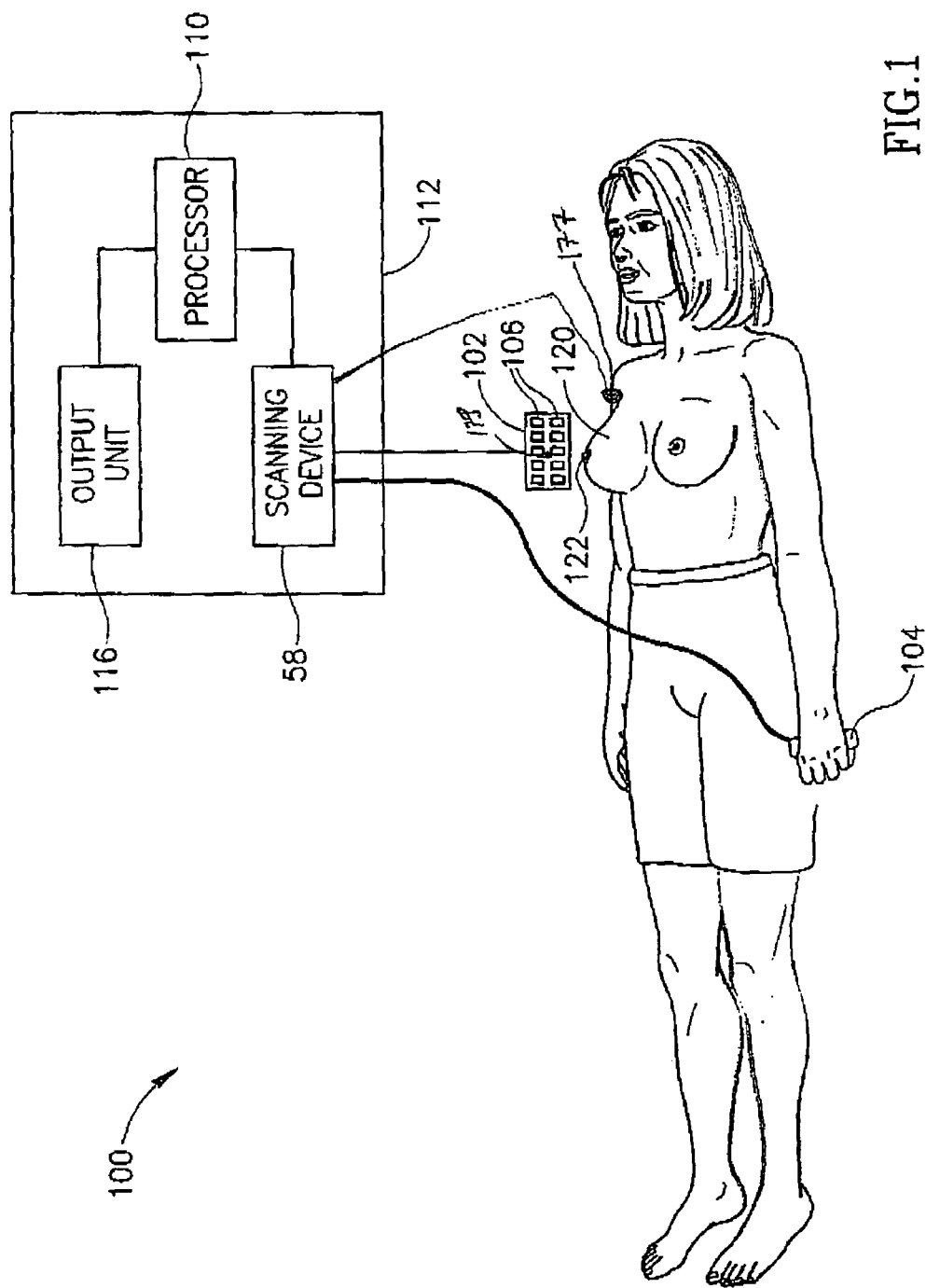
FIG. 1 is a schematic illustration of a breast examination system 100, in accordance with an exemplary embodiment of the present invention.

FIG. 1 is a schematic illustration of a breast examination system 100, in accordance with an embodiment of the present invention. Breast examination system 100 comprises an electrode 104 adapted to apply electrical signals to a patient and a surface probe 102 adapted to sense electrical signals, induced by the applied signals, from a breast 120 of the patient. Electrode 104 may comprise, for example, a hand held cylinder which is held by the patient and provides electrical signals to the patient through the hand. Surface probe 102 optionally comprises a multi-element probe which includes, for example, a two dimensional array of sensing elements 106. In an exemplary embodiment of the present invention, surface probe 102 comprises a square 8×8 or 16×16 array of sensing elements. Alternatively, surface probe 102 comprises a rectangular array of sensing elements. The use of a square or rectangular array of sensing elements allows simple correlation between the sensing elements and a rectangular generated image. Further alternatively, the elements of surface probe 102 are organized in other shapes, for example in a circular shape. The probe is not shown positioned on the patient for clarity. However, in exemplary embodiments of the invention, the probe is positioned on the front of the breast, covering the nipple.

In some embodiments of the invention, system 100 further comprises an electrical impedance scanning device 58 which controls the sensing of the impedance signals by sensing elements 106 and/or the applying of electrification signals to the patient from electrode 104. Scanning device 58 may be substantially any suitable electrical impedance scanning device known in the art, for example, a T-Scan™ 2000 Impedance Scanner marketed by TransScan, Israel, or any of the scanners described in U.S. Pat. Nos. 5,810,742, 4,458,694, PCT applications PCT/IL00/00127, PCT/IL00/00839 and/or U.S. patent application Ser. No. 09/460,699, the disclosures of which documents are incorporated herein by reference.

A processor 110 optionally receives the signals sensed by sensing elements 106 and determines therefrom, a malignancy score of breast 120, as described below. An output unit 116 optionally provides an indication of the malignancy score to the physician and/or to the patient. In some embodiments of the invention, output unit 116 provides a binary score. Optionally, output unit 116 includes an indicator which lights up, for example, an indicator light, optionally when additional tests are required. Alternatively or additionally, output unit 116 includes different color indicators, which indicate different test results. For example a green light may indicate that additional tests are not needed and a red light indicates that additional tests are required. In some embodiments of the invention, output unit 116 includes a LED display that states, for example, "additional tests" or "OK", as appropriate. Alternatively or additionally, output unit 116 includes other output interfaces, such as a speaker that provides sound indications. Alternatively or additionally, the malignancy score is selected from a multi-value scale and output unit 116 provides the value of the malignancy score, for example on a LED display.

In an exemplary embodiment of the invention, the malignancy score does not indicate the location a possible anomaly. In some embodiments of the invention, system 100 does not attempt to determine the location of an anomaly but only to provide a general indication as to whether such an anomaly exists.

In some embodiments of the invention, processor 110 is included in a single housing 112 with surface probe 102, output unit 116 and impedance scanning device 58. Optionally, housing 112 includes a socket adapted to connect to electrode 104. In some embodiments of the invention, housing 112 includes a compartment adapted to receive electrode 104 when not in use. Alternatively to including surface probe 102 in housing 112, housing 112 includes a socket adapted to connect to surface probe 102. Thus, the replacement of surface probe 102 is simplified, for example, if one-time surface probes 102 are used. Further alternatively, surface housing 112 includes a permanently connected cable for attachment to surface probe 102 or permanently connected to surface probe 102.

Optionally, system 100 is light weight and/or portable, allowing simple movement of the system between locations. In some embodiments of the invention, housing 112 requires a relatively small space volume, such that it may be used, for example, in every physician's office, without requiring a large amount of storage space. System 100 is optionally of relatively low cost to further facilitate its wide distribution.

It is noted that the tests performed using system 100 do not use ionizing radiation and are not significantly painful. Therefore, these tests are not expected to be objected to by patients. By having system 100 widely distributed, for example, in every women physician's clinic, the tests of system 100 may be applied to a relatively large percentage of the population, which visits physicians for periodic checkups and/or for other reasons.

Figure 2:
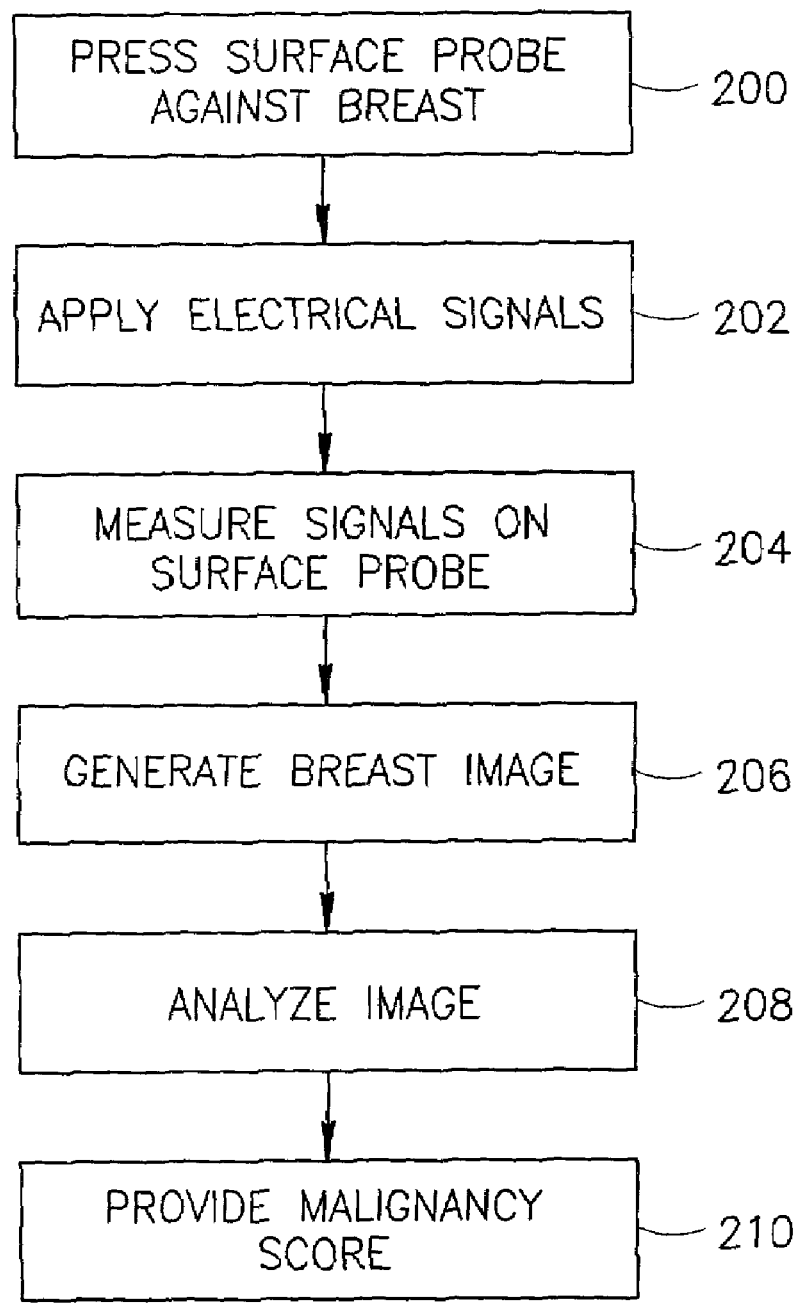
FIG. 2 is a flowchart of acts performed during a cancer scanning procedure, in accordance with an exemplary embodiment of the present invention.

FIG. 2 is a flowchart of acts performed during a cancer scanning procedure, in accordance with an embodiment of the present invention. Surface probe 102 is pressed (200) against a surface of breast 120, including the nipple (marked 122 in FIG. 1). Electrical signals are applied (202) through electrode 104 to the patient, optionally from a body surface remote from breast 120. Applying the electrical signals from a remote point, makes the electrical signals reach surface probe 102 substantially orthogonal, as from infinity. Signals on surface probe 102 formed responsive to the applied signals are measured (204). According to the measured signals, admittance values corresponding to each of sensing elements 106 is calculated, so as to generate (206) an image of the breast. The calculated admittance value optionally includes the real admittance. Alternatively or additionally, a complex admittance value and/or other dielectric parameters are calculated for each pixel. The generated image is analyzed (208) and a malignancy score is provided (210) by output unit 116 based on the analysis.

Providing a malignancy score, rather than an image which is to be analyzed by a physician, makes system 100 simple for operation. The simplicity of system 100 allows wide use of the system, for example by every women physician and/or by nurses.

Referring in more detail to pressing (200) surface probe 102 against a surface of breast 120, in some embodiments of the invention, probe 102 is pressed against a surface that includes nipple 122 and at least a predetermined number of pixels (e.g., 3-4) in each direction around the nipple. Alternatively or additionally, probe 102 is pressed against a surface that includes an area not including the nipple, optionally of a size at least of the nipple. The image generated from this area is optionally used for comparison to the signals received from the nipple, as described hereinbelow.

The measuring of the admittance from nipple 122, provides a better indication of the malignancy of the breast, at least partially due to the lower impedance of the nipple relative to other outer surfaces of the breast. By having a lower impedance, nipple 122 attracts currents from throughout the breast, thus providing from a single point an indication on the entire breast. Additionally, the high surface impedance of the skin, which generally masks the tissue impedance for low frequencies, is at least partially avoided.

Furthermore, nipple 122 is at one end of the ducts. Since most cancers start at the ducts or the lobula, nipple conductivity is a good example of breast condition. In some embodiments of the invention, surface probe 102 includes a marking defining a point that is to be placed on the nipple.

Optionally, a circular probe with a narrow guard ring is used to limit the measurements to the nipple. Preferably, this probe is placed on the areola. Alternatively or additionally, an annular probe, i.e., one having a ring electrode is used as a standardized probe which covers only an annular portion of the nipple, i.e., a portion of the areola. In some embodiments a probe having a depression at the tip of the nipple is used. This reduces or avoids the pressing of the nipple into the breast. While the tip is thus not generally imaged, the amount of the areola that is imaged is greatly increased. The probe may include an imaging capability to aid in placement. Alternatively, the probe is a single electrode probe and the score is determined based on the impedance measured by the single electrode. In some embodiments of the invention, a voltage is applied to the guard ring to at least partly cancel the cupping.

Optionally, a disposable gel interface, for example as described in PCT patent publication WO 01/64102, entitled Uniform, Disposable, Interface for Multi-Element Probe (the disclosure of which is incorporated by reference) is placed between probe 102 and breast 120, so as to provide good electrical contact between probe 102 and breast 120, while preventing direct contact between the probe and the breast, allowing safe use of probe 102 with a plurality of patients. Alternatively or additionally, probe 102 comprises a disposable breast interface, as described for example in U.S. Pat. No. 5,810,742 to Pearlman. Further alternatively or additionally, probe 102 in its entirety comprises a disposable probe, which is replaced for each patient. In some embodiments of the invention, probe 102 is cleaned and/or sterilized between test procedures.

Referring in more detail to applying (202) the electrical signals, in some embodiments of the invention, the electrical signals comprise AC signals at a single frequency. The frequency of the applied signals is optionally selected as a frequency at which a relatively high (or highest) response value difference is expected between a healthy breast and a cancerous breast. Other frequency schemes, as described below may be used.

Figure 3A:
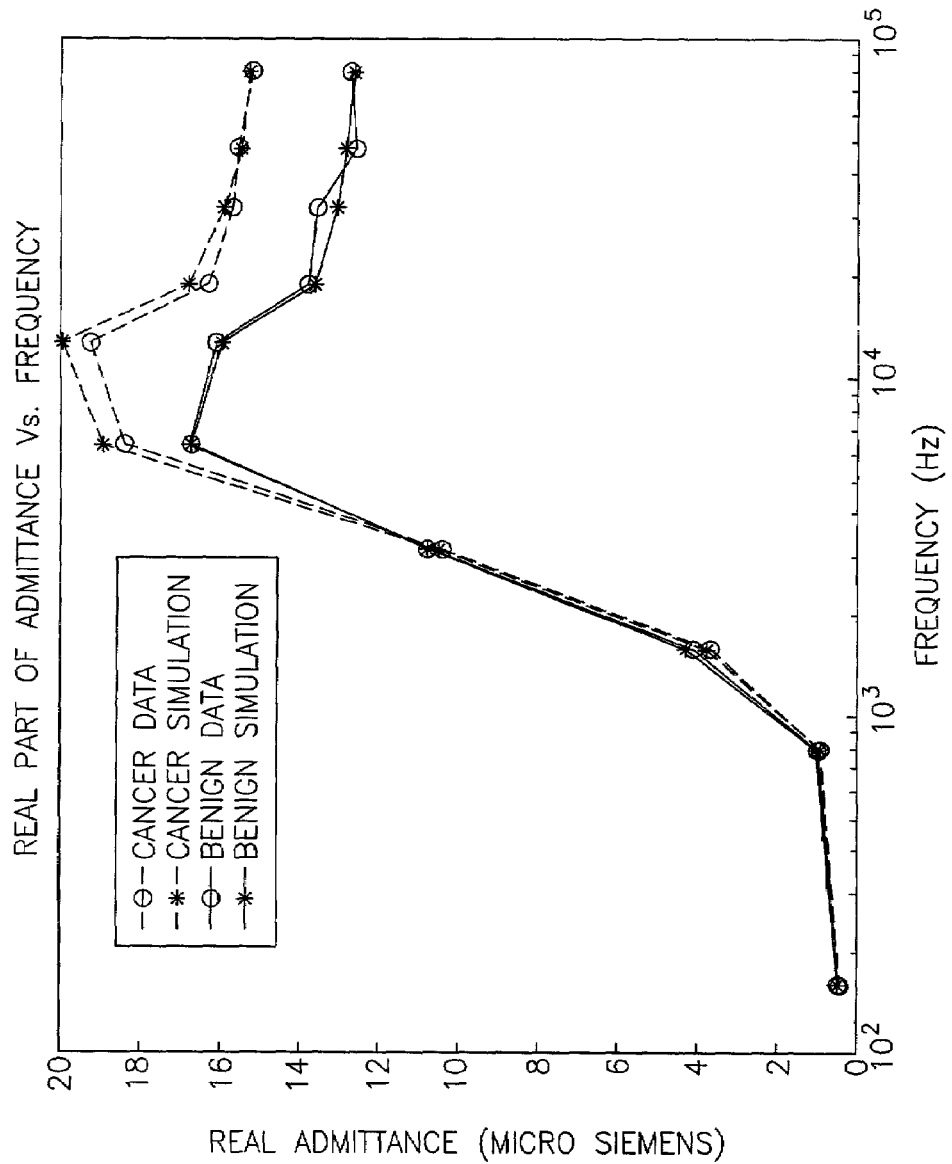
FIGS. 3A and 3B are schematic comparative graphs of the real and imaginary admittance of healthy and cancerous breasts, based on simulations and field tests.

FIG. 3A is a schematic comparative graph of the real admittance of healthy and cancerous breasts, based on simulations and field tests. As indicated on the figures, the curves represent the real admittance in field tests for healthy and cancerous breasts, respectively and the real admittance in simulations for healthy and cancerous breasts, respectively. The simulations were performed under the assumption that the breast has a uniform inner tissue impedance and a high impedance value for the skin throughout the breast, except around the nipple, where a lower impedance value is assumed. For healthy breasts, a value of 10 ohm/meter was used in the simulations, while for cancerous breasts a value of 12 ohm/meter was used. The higher impedance is generally due to an increase in the estrogen concentration within the breast and/or to an increase in the blood volume, due to neovascularization.

As can be seen from a comparison of the curves, for frequencies above about 100 kHz, there is a distinct difference in the real admittance between cancerous and non-cancerous breasts.

Figure 3B:
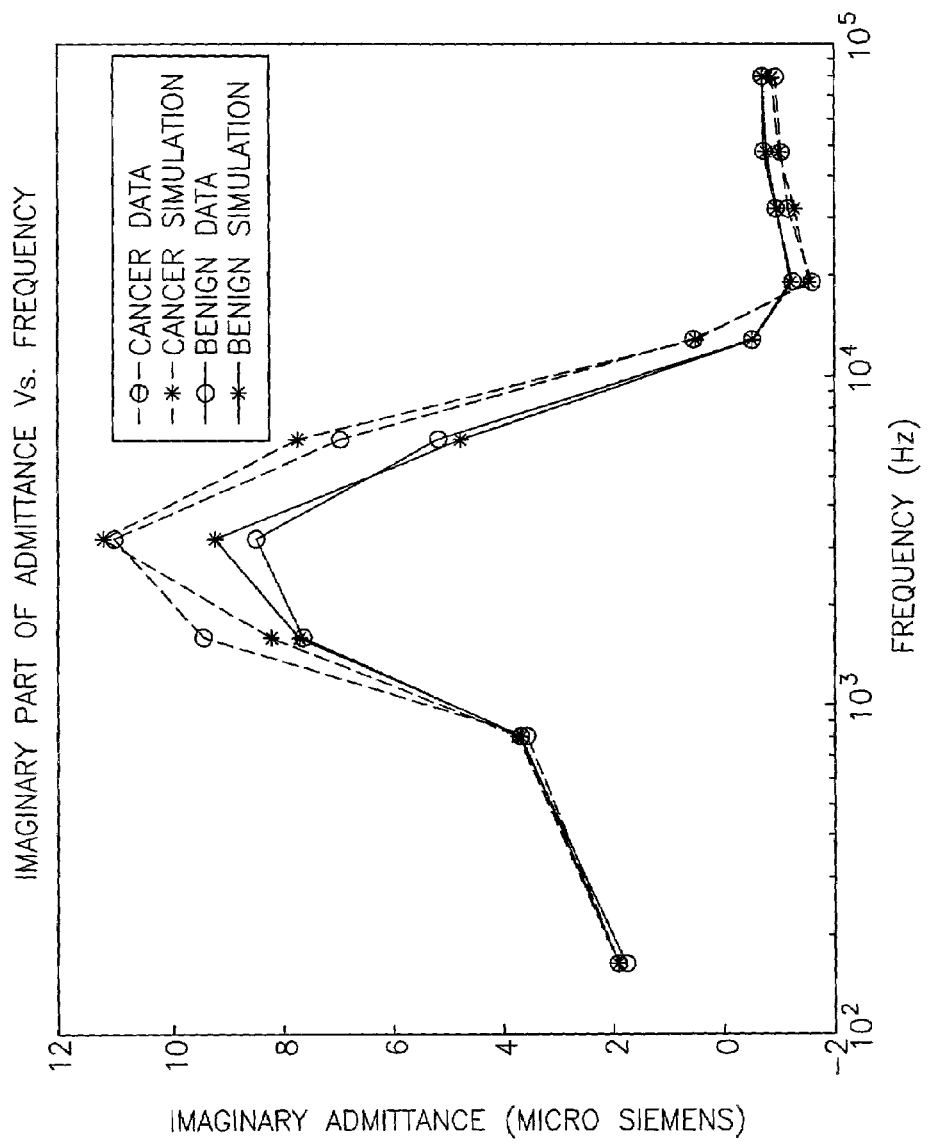

FIG. 3B is a schematic comparative graph of the imaginary part of the admittance of healthy and cancerous breasts, based on simulations and field tests. As indicated on the figure, the curves represent the imaginary part of the admittance in field tests for healthy and cancerous breasts, respectively and the imaginary part of the admittance in simulations for healthy and cancerous breasts respectively. As can be seen from FIG. 3B, at frequencies between about 1-10 kHz, there is a distinct difference between the capacitance of cancerous and non-cancerous breasts.

In some embodiments of the invention, the applied (202) electrical signals are at a single frequency so as to allow for simple apparatus which is accurately tuned for a single frequency. Optionally, a frequency of about 100-150 kHz is used, so as to enjoy the distinctness in both the real admittance and the capacitance. Alternatively, a frequency in which a highest distinctness of the real admittance is expected is used. Further alternatively, a lowest frequency with a sufficient expected distinctness is used, as apparatus for operation with lower frequencies is generally simpler and/or cheaper. Further alternatively, as discussed below, signals at a plurality of frequencies may be used. Further alternatively, the results for several frequencies are combined.

Referring in more detail to analyzing (208) the generated image (206), in some embodiments of the invention, an area of the image corresponding to the nipple is determined. Optionally, the area corresponding to the nipple is determined according to its admittance values which are generally different than values received in other areas of the breast. In some embodiments of the invention, the generated image is searched for an area which has a highest correlation to an expected pattern of the nipple.

Alternatively or additionally, the area corresponding to the nipple is determined as an area covered by predetermined pixels corresponding to the marking on surface probe 102, which is placed on the nipple by the physician. In some embodiments of the invention, the area of the nipple is determined based on both the admittance values and the surface probe marking. Further alternatively or additionally, other methods are used to determine the area of the image corresponding to the nipple, for example acquiring an image of the breast with the probe thereon or receiving an indication from the physician.

In some embodiments of the invention, an average real admittance value is determined for the nipple. Optionally, the average is determined over all the pixels determined as corresponding to the nipple. In some embodiments of the invention, the same weight is given in the average to all the pixels of the nipple. Alternatively, different weight is given to different pixels, for example, greater weight may be given to values of pixels closer to the center of the nipple. In some embodiments of the invention using this alternative, the size of the nipple on the image is not determined, as the decreasing weights limit the affect of measurements far from the center of the region. In other embodiments of the invention, the determination of the nipple area is used to find the center of the nipple.

Optionally, the average nipple admittance value is divided by an average non-nipple admittance value, so as to provide a normalized average nipple admittance value. In some embodiments of the invention, the values of all the pixels not corresponding to the nipple are included in the non-nipple admittance average, with equal or different weights (e.g., according to distance from the nipple). Alternatively, only pixels distanced from the nipple area by a predetermined number of pixels are used in the average. Further alternatively or additionally, a non-nipple breast area, optionally of about the size of the nipple, is found, and the average admittance value of this area is used in the normalization. The non-nipple breast area is optionally found according to the admittance values of the area. For example, an area with smooth values (i.e., without sharp changes of values between pixels) may be chosen.

Alternatively or additionally, an electrical response to signals applied from electrode 104 is measured at one or more points in the vicinity of the nipple optionally on the breast, and an average of the measured signals is used to normalize the average nipple admittance value. The normalization prevents the average nipple admittance value from reflecting the admittance of the path from electrode 104 to the breast.

In some embodiments of the invention, an additional probe (not shown) is used to measure the voltage used in the impedance determination. The use of such an additional probe allows measurement of the voltage at a location not affected by the current sensing elements 106, which may have a zero voltage for the measurement. Alternatively or additionally, one or more of sensing elements 106 are adapted to measure voltages, i.e., have a high input impedance. Optionally, while the current sensing elements 106 measure currents, which are used to determine the real admittance, the voltage sensing elements sense a voltage used in the normalization.

Optionally, the breast signals are measured in response to the same applied signal as used for inducing the measured image or impedance measurement. Alternatively or additionally, the breast signals are measured in response to a different applied signal, for example applied at a different time, with a different frequency and/or from a different electrode than electrode 104.

Alternatively or additionally, any other normalization methods are used, for example those described in U.S. patent application Ser. No. 10/033,017, entitled Diagnosis probe, filed Oct. 22, 2001, the disclosure of which is incorporated by reference.

Further alternatively or additionally, the electrical signals from electrode 104 are applied from a point near the breast, so that the currents are applied close to surface probe 102 and are not attenuated by a long path. Optionally, electrode 104 is placed substantially opposite surface probe 102, for example on the back of the patient, so that currents from the electrode flow substantially evenly to elements 106. Alternatively or additionally, electrode 104 is placed on a surface of the breast not necessarily opposite surface probe 102. In some embodiments of the invention, electrode 104 comprises a single electrical interface for applying electrode signals. Alternatively, electrode 104 comprises a multi-element probe, which allows applying electrical signals in a pattern, as described for example in PCT publication WO 01/43630, entitled Localization of Anomalies in Tissue and Guidance of Invasive Tools Based on Impedance Imaging, the disclosure of which is incorporated herein by reference.

In some embodiments of the invention, the electrical signals are applied from a ring placed around the base of breast 120. Alternatively, the effects of the surface impedance of the current source are neutralized by measuring the voltage at a point intermediate the current source and the breast. For example, the current source is applied by a probe held in one hand and the "applied" voltage is measured using a probe on the shoulder, along the arm or between the breasts.

Optionally, as indicated above, the malignancy score comprises a binary value. In some embodiments of the invention, if the normalized average nipple admittance value is above a predetermined value, the malignancy score is set to a value indicating that farther tests are required. Alternatively, the normalized average nipple admittance value is transformed to a multi-value malignancy scale, according to medical tests performed on healthy and malignant breasts. For example, the scale may range between one to ten or one to one hundred. In some embodiments of the invention, the different score values indicate the urgency of performing additional tests and/or the nature of such tests. Optionally, the scores are outputted as short messages which indicate the further acts required, if any. In an exemplary embodiment of the invention, different messages are used suggesting when additional tests are required, e.g., immediately, within half a year, in a year, etc.

In some embodiments of the invention, in the development of system 100, medical tests are performed on a group of healthy women to determine values of one or more parameters for each woman. At a later time, according to a determination of which of the women developed cancer, the values of the one or more parameters are correlated to the malignancy scores (e.g., cancerous, non-cancerous). System 100 is accordingly calibrated to indicate a possible malignancy based on these later clinical findings. Such results may be further segmented according to the age and/or hormonal state of the patient, the size of the breast and/or the nipple and/or other physical characteristics of the patient.

Alternatively or additionally, medical tests are performed on breasts including cancer and on breasts known not to include cancer. In some embodiments of the invention, a breast is considered as not including cancer according to x-ray, ultrasound, MRI and/or other tests. Alternatively or additionally, a breast is considered not including cancer at the time of the test if no signs of cancer are found a predetermined time after the tests, e.g., after a year.

In some embodiments of the invention, the output indication is calibrated so as to achieve a relatively low false negative ratio even at the expense of a relatively high false positive ratio. The women identified falsely as requiring additional tests will be directed to tests which in accordance with current procedures they would have been required to do in any event. Alternatively, the output indication is calibrated to achieve a relatively low false positive ratio even at the expense of additional false negatives, so as to limit the number of women sent unnecessarily to additional tests. It is noted that the output indication provided relates to cancer probability and a negative answer is not to be understood as indicating absence of cancer.

In some embodiments of the invention, system 100 is used as a first examination unit on breasts not yet examined by other imaging or diagnostic equipment. In an exemplary embodiment of the invention, system 100 is calibrated to send about 5% of the scanned women to additional tests. For these embodiments, it is expected that between 25-50% of the patients with a cancerous breast will be sent for additional tests. These figures can be compared to present clinical breast exams, Ultrasound Examinations and Mammography, which together find 85% of breast cancers. The present examination has the same approximate range of specificity and false positives as palpation alone. It can thus be used as a stand alone screening procedure for younger women in low risk groups or, preferably, in conjunction with palpation to improve the chances of finding early cancers or pre-cancerous conditions. In general, patients who test positive in the described impedance scan (and/or in the palpation, if performed) would be sent for further testing, as appropriate.

Alternatively to generating (206) the image from real admittance values, in some embodiments of the invention, each pixel has a value that represents the complex admittance, the real or complex impedance and/or any other dielectric parameter. In some embodiments of the invention, the dielectric parameter comprises a phase of the signals sensed at each pixel.

In some embodiments of the invention, the pixel values represent a polychromatic measure, which depends on measurements in a plurality of frequencies, such as described in U.S. Pat. No. 5,810,742 to Pearlman. Optionally, electrical signals are applied at a plurality of frequencies and response signals are measured for each of the frequencies. An indicator frequency (designated herein $\omega_c$) at which the imaginary admittance (Im(Y)) reaches a local maximum, is determined. The indicator frequency is optionally used in generating the malignancy score, as the indicator frequency $\omega_c$ is generally different for healthy and malignant tissue. Generally, the measured imaginary admittance at low frequencies is due to the skin admittance whose imaginary portion increases with the frequency. Between about 1-10kHz, the imaginary admittance reduces due to a "discharge" of the skin capacitance through the tissue which still has a generally real impedance. The frequency at which this discharge occurs is indicative, in some cases, of the health of the tissue. Generally, the indicator frequency $\omega_c$ is proportional to $G_b/C_s$. Therefore, in malignant tissue, the indicator frequency $\omega_c$ is at a higher frequency than in healthy tissue.

Optionally, the indicator frequency $\omega_c$ is determined separately for each pixel of the maps. Alternatively or additionally, a single indicator frequency is determined for all the pixels of the maps, by averaging the pixel indicator frequencies or by averaging the measured impedance values before determining the indicator frequency.

In an exemplary embodiment of the invention, the scanner utilizes three or four frequencies to provide an image of the breast. Generally, low frequencies are used for this image. The image is used to determine the extent of the nipple. Then, in a second phase, a preset frequency group is used to acquire data which can be used to determine the admittance of the nipple (which may be limited to all or a portion of the areola) and to determine normalization values from the surrounding tissue. Preferably, the admittance or other characteristic value used in finding the score is the underlying admittance of the internal tissue. In this embodiment the score is based, on a frequency (($\omega_c$) at which the real or imaginary part of the admittance is highest.

In a further embodiment of the invention, a frequency ($\omega_c$) or frequencies specific to the patient are used to determine the score of the particular patient. In particular, such frequencies may be one or more of the frequency of maximum imaginary part of the admittance, the frequency of the maximum value of the real part of the admittance or other frequencies that are characteristic of the particular frequency response of the particular breast. This frequency may be determined by curve fitting over a series of closely spaced frequencies or by scanning or by using a value for one of the closely spaced frequencies that has the characteristic.

In some embodiments of the invention, the score is based on the phase of the admittance at the indicator frequency. In some embodiments it is based on the normalized (for example, to non-nipple areas, as described above) real part of the impedance. In some embodiments it is based on the normalized imaginary part of the admittance. In some embodiments it is based on the magnitude of the indicator frequency ($\omega_c$). In some embodiments it is based on the amount of cupping. In some embodiments the score is based on a combination of these characteristics. Applicants have found that the phase alone provides a good indicator that can be used for the score.

Optionally, for each characteristic a separate score is determined and the malignancy score is determined as a weighted sum of the separate scores. Alternatively, the malignancy score is a composite function of the separate scores. In an exemplary embodiment of the invention, the plurality of separate scores comprise real admittance values (or other characteristics) for a plurality of frequencies. Alternatively or additionally, the plurality of separate scores comprise a plurality of the above described dielectric measures, for a single frequency or for a plurality of frequencies. Further alternatively or additionally, one or more of the dielectric parameters is measured for a plurality of different breast conditions, for example with different compression levels of the breast.

In some embodiments of the invention, one or more of the characteristics is based on a change function of the measured impedance signals over time, for example a change function of changes due to the heart cycle. Optionally, the determination of the pulsatile changes is performed using any of the methods described in Israel Patent application number 143374 filed May 24, 2001 and entitled Anomaly Detection Based On Signal Variations, the disclosure of which is incorporated herein by reference.

Alternatively or additionally to determining the malignancy score as a predetermined weighted sum of the measure scores, the weights of some or all of the measure scores are determined responsive to the distinctness (i.e., having a high contrast between nipple and other areas) Optionally, the nipple descriptors are normalized by factors taken from different sectors (non-nipple sectors) of maps generated for the measures. For example, a plurality of maps may be generated for the different measures and the malignancy score is determined based on a map selected as a best map, e.g., a most distinct map or one with a low noise or a high signal to noise ratio. Alternatively or additionally, the best map is selected as the map with a highest average nipple score.

In some embodiments of the invention, the amount of cupping is determined by the following method. The capacitance C and conductance G values of a plurality of maps are averaged, to receive average values C and G for each map. The average values of G/C as a function of the frequency are optionally fit into a parabola $A\omega^2+b$. The reciprocal of A is optionally taken as the indicator frequency $\omega_c$. In some embodiments of the invention, the parabola is generated using maps of relatively low frequencies, e.g., 100-1000 Hz, such that the maps do not substantially suffer from cupping. In an exemplary embodiment of the invention, maps for 100, 200 and 1000 Hz are used. Alternatively or additionally, a cupping effect canceling method is applied to one or more of the maps before averaging its values. In some embodiments of the invention, the cupping effect canceling method includes fitting the measured signals into a paraboloid and removing the values of the fitted paraboloid from the measured data.

Further alternatively or additionally, the measured admittance values for the plurality of frequencies are fit into a model which correlates between an unknown inner tissue admittance and the measured admittance values, as a function of frequency, in order to estimate the inner tissue admittance. The malignancy score is then determined as a function of the estimated inner tissue admittance, based on a theoretical model, lab tests and/or clinical tests.

In some embodiments of the invention, the frequencies determined are in the range of about 100 Hz-10 KHz. Alternatively, the measurements are performed over a large span of frequencies, so as to gather as much data as possible. Optionally, the range of frequencies used is limited by the cost of the apparatus used. In an exemplary embodiment of the invention, system 100 is provided in different models according to a tradeoff of cost and frequency span. In an exemplary embodiment of the invention, a span of frequencies between about 100 Hz and 10 MHz is used.

Optionally, in these embodiments, electrode 104 applies a composite electrical signal which includes a plurality of frequencies. The signals sensed by surface probe 102 are optionally decomposed into separate frequencies, corresponding to the applied frequencies of the composite signal. Alternatively or additionally, electrode 104 comprises a plurality of separate electrical leads which apply signals at different frequencies to the patient. Further alternatively or additionally, during a test session, electrode 104 applies at different times signals of different frequencies and sensing elements 106 sense signals responsive to the applied signals.

In some embodiments of the invention, measurements at different frequencies are used for determining the area of the nipple and the impedance of the nipple. Alternatively or additionally, determining the impedance of the normalization area and/or finding the normalization area are performed with frequencies different from that used for determining the area of the nipple and/or the impedance of the nipple. Optionally, for each task, a frequency which is expected to have a largest contrast for that task is used.

Alternatively to generating a map and determining from the map the average admittance value, a single admittance value is measured, for example from a point on the nipple or over an area of the nipple. In some embodiments of the invention, signals are measured at a predetermined number of points and the values at these points are used in determining the average admittance from the nipple.

In some embodiments of the invention, instead of the malignancy score running on a single scale, the malignancy score has a plurality of scales. For example, the malignancy score may include a first indication of whether the breast is cancerous and a second indication which represents the susceptivness of the breast to changes, e.g., the next time in which tests are required.

In some embodiments of the invention, tests are performed for both breasts of the patient and the results of the breasts are compared. Optionally, the malignancy score is given a high value when there are substantial differences between the measurements of the breasts. Optionally, the scores for the breasts are averaged or summed or weighted summed to give a single score. Optionally or additionally, a balance between the scores of the two breasts is determined. If one of the breasts has a much higher value than the other, the site of a malignancy may be indicated. Optionally or additionally, the value of the score for the breast with the lower score is subtracted from the score of the other breast (or the scores are divided). This is especially useful where one breast has a low score to provide normalization of the high score to improve the accuracy of the determination. Since each of these methods may indicate a different balance of indications or source of an anomaly, more than one of scores indicated above are determined and each is measured against its own threshold. Optionally, a positive indication is given when one or more of the scores is above its threshold. Optionally, a combined score, based on a weighting of the scores can be used.

As indicated above, the malignancy score may be determined based on the total admittance (or other characteristic) as determined directly from the measured signals. The malignancy score may, alternatively or additionally, depend on the relative values of the pixels of the map. In an exemplary embodiment of the invention, the malignancy score may depend on the size and/or shape of high admittance areas. In other embodiments, for example as is now described, the measured signals are used to estimate an internal body tissue admittance, or any other body tissue dielectric parameter. The malignancy score is then determined, at least partially, based on the tissue admittance. Thus, the effect of the skin impedance is separated from the tissue impedance and a more accurate malignancy indication may be received. It is noted that other methods than is now described may be used to reduce the effect of the skin and that in some cases, as described above, an indication may be provided without eliminating the effect of the skin, for example when relatively high frequencies are used. In other embodiments of the invention, the effect of the skin adds to the malignancy score, as for certain frequencies changes in the skin due to the malignancy may be determined.

Figure 4:
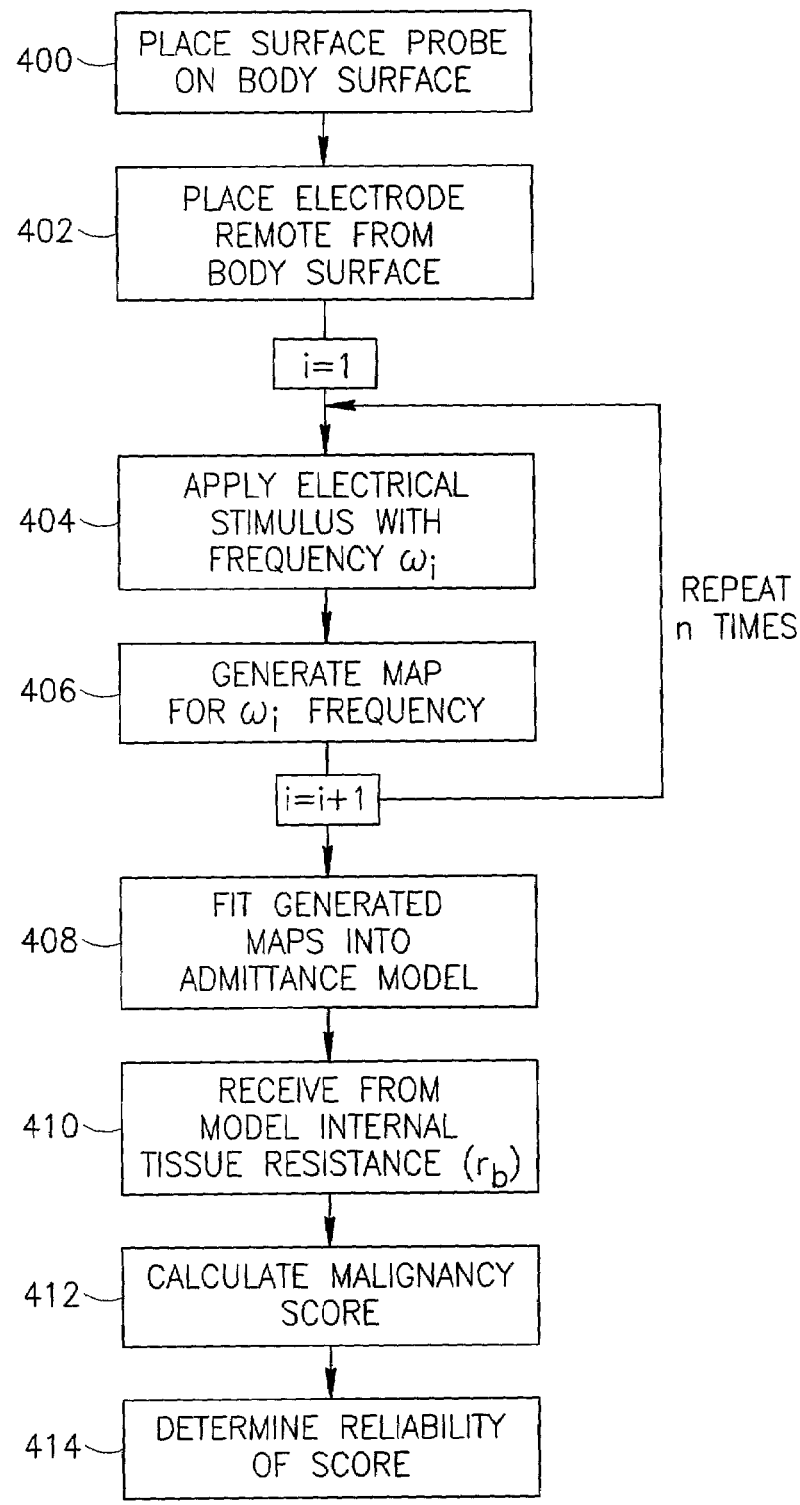
FIG. 4 is a flowchart of acts performed in a tissue analysis procedure, in accordance with another exemplary embodiment of the present invention.

FIG. 4 is a flowchart of acts performed in a tissue analysis procedure, in accordance with another exemplary embodiment of the present invention. Surface probe 102 is placed (400) on a first surface of a breast (on the nipple, close to the nipple or remote from the nipple) to be analyzed. Electrode 104 is optionally placed (402) on a body surface remote from the analyzed body portion 120. In some embodiments of the invention, an electrical stimulus at a first frequency is applied (404) to electrode 104. Optionally, sensing elements 106 are held at an equipotential level and a voltage electrical signal is applied to electrode 104 relative to the equipotential. Responsive to the stimulus, electrical current signals are optionally sensed by elements 106 of surface probe 102, so as to generate (406) a surface map ($M_f$) of the body portion. The application (404) of an electrical stimulus and generation (406) of a respective surface map is repeated for at least one additional frequency, so as to generate n maps. As described hereinbelow, in some embodiments of the invention, additional surface maps at additional, different, frequencies are generated in order to increase the accuracy of the determination of the internal tissue impedance. The maps may be generated concurrently and/or one after the other, as described above.

In some embodiments of the invention, in generating maps $M_f$, the amplitude and phase of the current sensed by elements 106, are measured relative to the stimulus signal. Optionally, the generated surface maps $M_f$ include, for each of the sensing elements 106 (designated for example by their coordinates (x,y)), a complex admittance $Y=G+iC$, formed of a real admittance (i.e., conductance) component $G_{x,y}=Re(Y)$ and an imaginary admittance component $C_{x,y}=Im(Y)/\omega$. C, G are calculated from the measured currents using any method known in the art, for example as described in U.S. Pat. Nos. 4,291,708 and/or 4,458,694, the disclosures of which are incorporated herein by reference.

The generated maps are optionally provided to processor 110 which fits (408) the values of the generated maps into a model of the admittance of the body portion, in order to determine (410) a real impedance (i.e., resistance) $r_b$ of the internal body tissue of body portion 120. An exemplary method for determining the real impedance from the generated maps is described hereinbelow with reference to FIG. 5.

In some embodiments of the invention, the resistance $r_b$ of the internal tissue is used to calculate (412) a malignancy score for the examined breast. Optionally, the malignancy score is a step function of an average of the internal tissue resistance values ($r_b$) over all the measured locations. In an exemplary embodiment of the present invention, the malignancy score has a binary value, which requires additional tests if the average of the internal tissue resistance values is below a predetermined value.

Many of the methods and alternatives described above with reference to FIG. 2, may be used also with respect to the embodiment of FIG. 4 and/or other embodiments of the invention. For example, any of the methods described above for applying stimulus of several frequencies and/or for generating maps from the generated signals may be used in the method of FIG. 4. For example, a plurality of frequencies may be applied together and measured together.

In some embodiments of the invention, before fitting (408) the maps into the model, the maps are preprocessed in order to remove serial impedance values corresponding to an extraneous path from electrode 104 to the breast, from the measured impedance values.

In an exemplary embodiment of the invention in which electrode 104 is held in the hand of the patient, the impedance of the extraneous path optionally includes impedance values due to the serial resistance of the hand, the pectorals muscle and the contact between electrode 104 and the hand. Optionally, the extraneous impedance is assumed to be equal for all the sensing elements and of a resistive nature. However, its value is uniform for all the pixels, thus it doesn't contribute to the cupping. This impedance can be neutralized by measuring the voltage at a point between electrode 104 and the breast, for example at the shoulder, upper arm or between the breasts.

The second element to be removed is the resistive breast tissue, which cause the cupping. Lastly, there is the skin, with parallel resistive and capacitive admittance. At low frequencies, it masks the cupping, and this masking decreases with frequency.

Therefore, each of the three elements of the path has special "fingerprint" and the frequency-dependent analysis can calculate the specific admittance of each.

Figure 5:
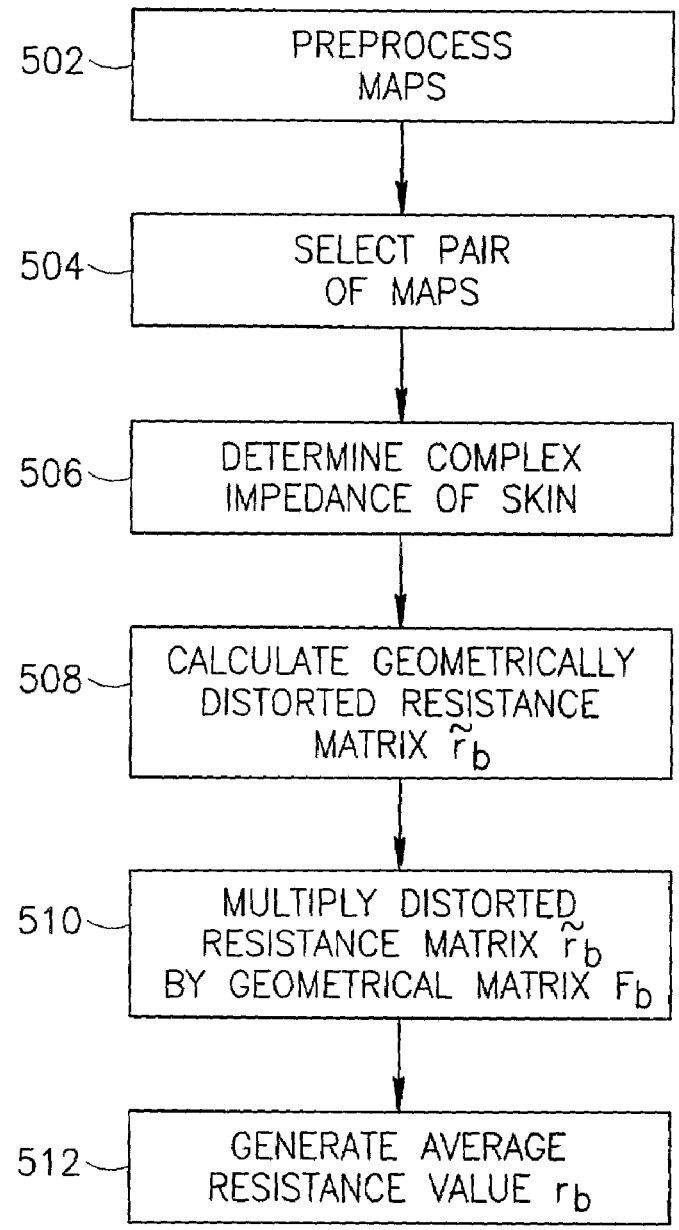
FIG. 5 is a flowchart of the acts performed in determining an internal body tissue impedance, in accordance with an exemplary embodiment of the present invention.
Figure 6:
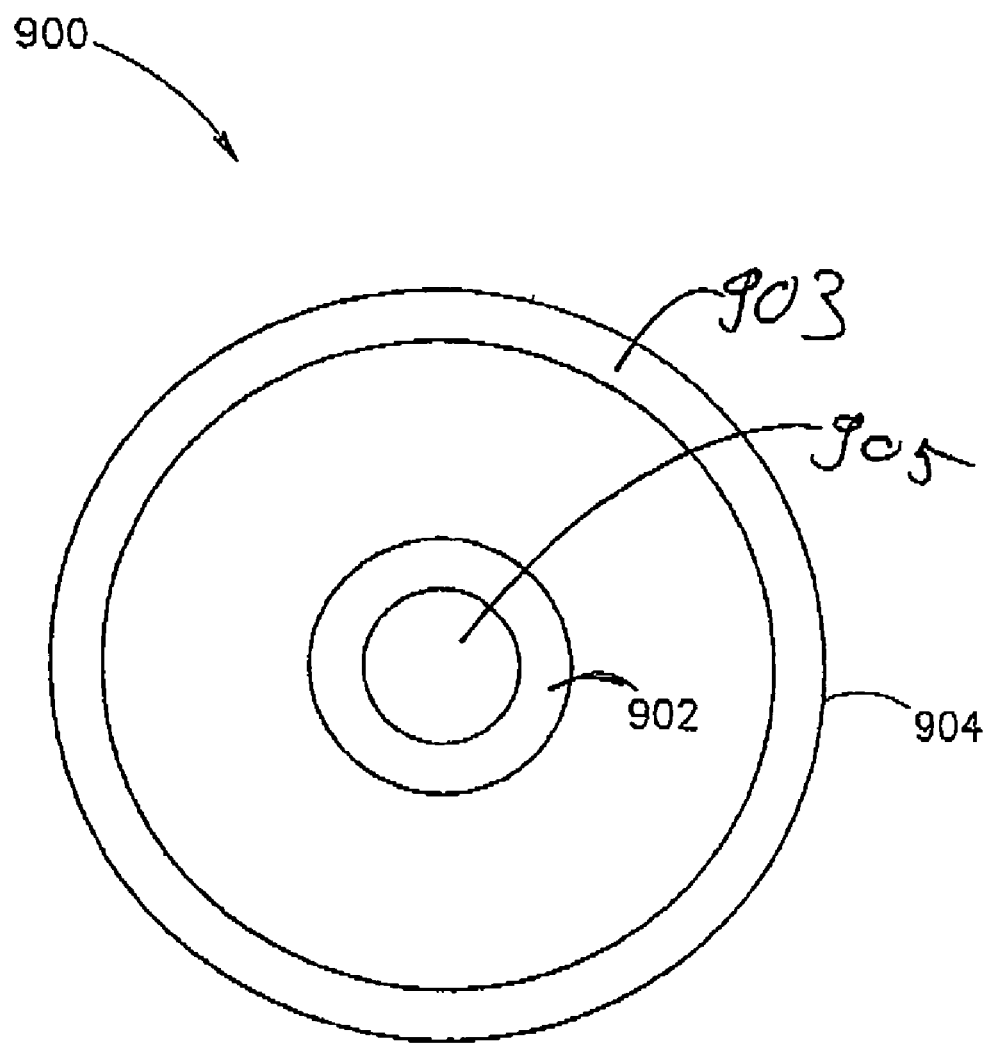

FIG. 5 is a flowchart of the acts performed by processor 110 in determining the internal body tissue impedance beneath surface probe 102, in accordance with an embodiment of the present invention. In some embodiments of the invention, processor 110 preprocesses (502) the surface maps ($M_f$), for better automatic evaluation of the maps. A pair of maps are optionally selected (504), for use in determining (506) a complex impedance of the skin.

In some embodiments of the invention, the skin impedance is determined (506) from a comparison of the measured admittance of the selected maps to a model of the expected admittance of the breast. Optionally, the complex impedance of the skin is determined from a comparison of the imaginary portion of the measured impedance at a plurality of frequencies to the respective imaginary portion of the model for the frequencies, under the assumption that the imaginary portion of the impedance of the body tissue is negligible. For relatively low frequencies this assumption is generally true, as the capacitance of the skin is much greater than of internal tissue. In some embodiments of the invention, the following equation is used for the two selected maps:

$$\text{Im}(Y_k^{-1}) = -\frac{\omega_k}{\omega_s} \frac{r_s}{1+(\omega_k/\omega_s)^2}, k = 1, 2 \quad (1)$$

in which $Y_{1,2}$ are values representing the selected maps, $\omega_{1,2}$ are the respective frequencies used in generating the maps, $r_s$ is the resistance of the skin and $\omega_s = 1/(r_s C_s)$, $C_s$ being the capacitance of the skin. In some embodiments of the invention, the values $Y_{1,2}$ representing the selected maps, used in equation (1), are averages of the values of all the pixels of the map. Alternatively, equation (1) is solved for each pixel separately, and/or for each group (e.g., rows, columns, rings) of pixels, separately. Final complex impedance values are optionally determined as a weighted average (or any other suitable function) of the impedance values from the solutions of equation (1) for different pixels and/or pixel groups.

In some embodiments of the invention, processor 110 calculates (508) a geometrically distorted resistance matrix $\tilde{r}_b$ of the internal body tissue beneath surface probe 102 based on a model of the admittance of the breast and the determined (506) complex impedance of the skin. Optionally, the calculation (508) of matrix $\tilde{r}_b$ is performed based on a comparison of the real portion of the measured admittance (G) to a model of the skin and body admittance, for example as in the following equation:

$$G = \text{Re}(Y^{-1}) = \tilde{r}_b + \frac{r_s}{1+(\omega/\omega_s)^2} \quad (2)$$

in which $r_s$ and $\omega_s$ have values from the determination (506) of the complex impedance of the skin. It is noted that in some embodiments, $\tilde{r}_b$ is a matrix which has a resistance value corresponding to measurements made at each of the elements of surface probe 102.

In some embodiments of the invention, geometrically distorted resistance matrix $\tilde{r}_b$ is assumed to be a product of a resistance matrix $\bar{r}_b$, representing the actual resistance of internal body tissue beneath the elements of surface probe 102, and a predetermined geometrical matrix $F_b$, which is representative of the geometry of surface probe 102. Alternatively or additionally, geometrical matrix $F_b$ is used to correct for the geometrical shape of the examined breast and/or for the routes of the electrical signals sensed by surface probe 102. Optionally, geometrical matrix $F_b$ cancels the cupping effect which appears due to the limited extent of surface probe 102. Processor 110 optionally multiplies (510) the geometrically distorted resistance matrix $\tilde{r}_b = F_b \cdot \bar{r}_b$ by an inverse of geometrical matrix $F_b$, so as to derive resistance matrix $\bar{r}_b$.

In some embodiments of the invention, a representative tissue resistance value $r_b$ is generated (512) from the resistance matrix $\bar{r}_b$. Optionally, the representative tissue resistance value $r_b$ is calculated as the average of the values of the elements of $\bar{r}_b$. Alternatively, the representative tissue resistance value $r_b$ is calculated as a weighted average of the values of the elements of $\bar{r}_b$. Further alternatively or additionally, the representative tissue resistance value $r_b$ is calculated based on the values of the resistance matrix $\bar{r}_b$ corresponding to specific regions, for example corresponding to the nipple.

Referring in more detail to preprocessing (502) the maps, in some embodiments of the invention, the surface maps ($M_f$) are spatially low pass or median filtered to smooth the maps. Thus, values in the map which are substantially different from their neighboring values, for example, because of an improper contact of one of the elements with the skin of the patient, are canceled. Alternatively or additionally, any other preprocessing methods known in the art for preparing images and/or maps for automatic analysis, are used.

Referring in more detail to selecting (504) a pair of maps, in some embodiments of the invention, the maps are selected according to the reliability of their values. Optionally, each map is assigned a reliability measure, for example based on its smoothness or signal to noise ratio. Optionally, the maps with the highest reliability measure are selected. In some embodiments of the invention, the selected maps ($M_f$) are chosen additionally based on the frequencies of the stimulation signals used in generating the maps, preferring for example a high frequency map if it is only slightly less reliable than a low frequency map. Optionally, the frequencies of the selected maps are separated by at least a predetermined bandwidth so that the maps provide substantially different information in determining the complex impedance of the skin. Alternatively or additionally, the maps generated based on the most separated frequencies, that have at least a predetermined reliability measure, are selected (504).

Alternatively or additionally to determining (506) the complex impedance of the skin based on a comparison of the measured signals to a suitable model, in some embodiments of the invention, the complex skin impedance is determined based on an analysis of the cupping effect appearing on one or more of the generated maps $M_f$. The term "cupping effect" refers herein to excessive currents sensed at the edges of maps $M_f$, due to the geometry of surface probe 102. In some embodiments of the invention, clinical tests, lab tests and/or simulations are performed in order to determine a correlation between different complex skin impedance values and the shape, size and/or extent of the cupping effect in impedance measurements of the breast. Optionally, processor 110 stores a table or function that correlates between different cupping effects and respective complex skin impedance values. In some embodiments of the invention, the cupping effect of each map is represented by one or more cupping parameters such as amplitude, diameter, extent and/or shape.

Optionally, for each map $M_f$, an intermediate complex skin impedance value is determined based on the cupping effect on the map, and the complex skin impedance is determined based on the intermediate values. Alternatively, a plurality of maps $M_f$ are fit together into a model, which states the expected cupping effect of the maps as a function of the complex skin impedance of the skin and the frequency, so as to determine the complex skin impedance. Performing the fitting based on a plurality of maps generally aids in differentiating between shapes on the map that are due to cupping effects and portions that are not related to the cupping effect.

In some embodiments of the invention, a guard ring is not used with surface probe 102 so as not to distort the cupping effects. Alternatively or additionally, a guard ring is used in determining one or more parameters of the cupping. Optionally, a signal with opposite phase from the stimulus signals applied by electrode 104, is applied to the guard ring. In some embodiments of the invention, the amplitude of the signal applied to the guard ring is varied to determine the amplitude required in order to cancel the cupping effect. This amplitude optionally serves as a numerical parameter of the cupping effect. In some embodiments of the invention, electrode 104 is placed orthogonal to surface probe 102 so as to maximize the cupping effect. Alternatively, electrode 104 is placed parallel to surface probe 102 so as to minimize the cupping effect.

Alternatively to using the cupping effect in determining the skin impedance, the cupping effect of matrix $\tilde{r}_b$ is used to evaluate the skin impedance value determined from equation (1). Optionally, the extent of the difference between distorted resistance matrix $\tilde{r}_b$ and an expected form of the matrix is used to correct the values of the determined skin impedance. For example, if the amplitude of the expected distortion is greater than the calculated distortion in $\tilde{r}_b$, the estimated value of the skin impedance is optionally slightly decreased. Distorted resistance matrix $\tilde{r}_b$ is then calculated again for the new skin impedance value. This process is optionally repeated until convergence or until the changes are smaller than a predetermined required consistency or delta value.

Referring in more detail to calculating (508) the geometrically distorted resistance matrix $\tilde{r}_b$, in some embodiments of the invention, matrix $\tilde{r}_b$ is calculated based on one of the maps in the pair selected for determining (506) the skin impedance $r_s$. Alternatively or additionally, the calculation (508) of matrix $\tilde{r}_b$ is performed based on a map different from those used in determining the skin impedance. Optionally, the calculation (508) of matrix $\tilde{r}_b$ is performed based on a relatively reliable map. In some embodiments of the invention, the calculation (508) of matrix $\tilde{r}_b$ is performed based on a relatively high frequency map ($M_f$), e.g., having a frequency of between about 5-20 kHz, such that the advantages of using a low frequency are still in effect, but the impedance masking of the skin is not too high. The use of a map $M_f$ from a relatively high frequency may also provide a map with a clear cupping effect, which as described above is used in some embodiments of the invention, in determining the skin impedance.

In an exemplary embodiment of the present invention, the skin impedance is determined (506) based on maps generated for frequencies of about 100 and 2000 Hz, and calculation (508) matrix $\tilde{r}_b$ is performed based on a map generated for about 5 kHz. Alternatively, determining (506) the skin impedance is performed based on maps generated for frequencies of about 100 and 5000 Hz, and calculation (508) of matrix $\tilde{r}_b$ is performed based on a map generated responsive to a stimulus signal of about 2 kHz.

In some embodiments of the invention, the calculation (508) of matrix $\tilde{r}_b$ is performed based on a plurality of maps ($M_f$), for which respective matrices are generated, and the final geometrically distorted resistance matrix $\tilde{r}_b$ is calculated as an average of the plurality of matrices. Alternatively, the result matrix is calculated as a weighted function of the respective matrices, in which higher weight is given, for example, to higher frequency matrices and/or to matrices based on more reliable maps. Further alternatively or additionally, the calculation (508) of matrix $\tilde{r}_b$ is performed using an over-determined problem solution method, based on a plurality of the generated maps ($M_f$).

Referring in more detail to geometrical matrix $F_b$, in some embodiments of the invention, geometrical matrix $F_b(x,y)$ is based on a theoretical model. In an exemplary embodiment of the invention, geometrical matrix $F_b(x,y)$ is calculated as an integral of the reciprocal of the distance from point $(x,y)$ to each of the pixels of the probe, for example using the following equation:

$$F_b(x, y) = \frac{1}{2\pi} \int \int dx' dy' \frac{1}{\sqrt{(x-x')^2 + (y-y')^2}} \quad (3)$$

Alternatively, geometrical matrix $F_b$ is generated empirically based on simulations and/or lab or clinical tests. In some embodiments of the invention, geometrical matrix $F_b$ is calculated separately for each patient. Optionally, before performing a breast examination procedure, surface probe 102 is placed on a uniform healthy body portion of the patient and one or more maps are generated, from which geometrical matrix $F_b$ is extracted for use in the examination procedure. The healthy body portion may be, for example, an area in the same breast remote from a suspected lesion and/or from the nipple and/or a point on the other breast. The measurements from the healthy body portion may be achieved using surface probe 102 and/or a different probe which is similar or identical to surface probe 102. In some embodiments of the invention, measurements are performed on both breasts, and the results with lower values are used in determining the geometrical matrix $F_b$ to be used for the breast with higher values.

Alternatively to using a predetermined value for geometrical matrix $F_b$, the fitting into equation (2) is performed, using a plurality of maps, under the assumption that matrix $F_b$ is unknown. Optionally, the fitting is performed under the assumption that matrix $F_b$ does not substantially change with frequency. Alternatively, the frequency behavior of the matrix is known (i.e., given $F_b$ for a first frequency it may be calculated for other frequencies). Optionally, the number of maps used is greater than the number of pixels in each map. Alternatively or additionally, the fitting is performed based on predetermined constraints on matrix $F_b$, such as assuming that groups of pixels in matrix $F_b$ have equal values.

Alternatively to determining resistance matrix $\tilde{r}_b$ and therefrom extracting the representative tissue resistance value $r_b$, the resistance value $r_b$ is calculated using a least square method directly from the map or maps used in the determination. In an exemplary embodiment of the invention, the resistance value $r_b$ is determined by integrating over the elements of the probe with the following equation:

$$r_b = \frac{\int dx dy \left[\text{Re}(Y^{-1}) - \frac{\omega_s}{\omega}\text{Im}(Y^{-1})\right]^2}{\int dx dy \left[\text{Re}(Y^{-1}) - \frac{\omega_s}{\omega}\text{Im}(Y^{-1})\right] F_b(x,y)} \quad (4)$$

In some embodiments of the invention, instead of using a single pair of impedance maps in the determination (506) of the complex impedance of the skin, the determination is repeated for a plurality of pairs of maps to provide respective intermediate skin impedance values. Optionally, the intermediate values are averaged in order to receive final skin impedance values. Optionally, the average comprises a weighted average, in which, for example, specific frequencies and/or more reliable maps are given higher weight.

Alternatively or additionally, the determination of the skin impedance is performed by fitting three or more maps into equation (1), using any over-determined equation solving method, such as the least square method.

Following is a discussion of the origin of equations (1), (2) and (4).

The impedance of body portion 120 is generally formulated by a sum of the complex impedance of the skin and the complex impedance of the internal body tissue. The complex impedance is generally modeled by a resistance in parallel with a capacitor. Hence, we receive:

$$Y^{-1} = \frac{1}{(r_b^{-1} + i\omega C_b)} F_b + \frac{1}{(r_s^{-1} + i\omega C_s)} F_s$$

where $F_b$ is a geometrical correction factor for the body impedance and $F_s$ is a geometrical correction factor for the skin impedance. As the skin is very thin, the geometry factor $F_s$ of the skin is assumed equal to 1. In addition, the imaginary admittance of capacitance $C_b$ of the internal body tissue at low frequencies is negligible. Hence:

$$Y = C + G = \left(r_b F_b + \frac{1}{r_s^{-1} + i\omega C_s}\right)^{-1},$$

or, using $\tilde{r}_b = F_b \cdot r_b$ and $\omega_s = 1/(r_s C_s)$:

$$Y^{-1} = \tilde{r}_b + \frac{r_s}{1 + i\omega/\omega_s} = \tilde{r}_b + \frac{r_s(1 - i\omega/\omega_s)}{1 + (\omega/\omega_s)^2}.$$

Separating this equation to real and imaginary portions, equations (1) and (2) are received.

By subtracting equation (1) from equation (2) we receive:

$$\tilde{r}_b = \left[\text{Re}(Y^{-1}) - \frac{\omega_s}{\omega}\text{Im}(Y^{-1})\right]$$

In some embodiments of the invention, equation (5) is used in the calculation (508) of matrix $\tilde{r}_b$ instead of equation (2).

Optionally, surface probe 102 has a size and shape such that the simplifications described above have a high reliability. In some embodiments of the invention, multi-element probe 102 has an area much greater than the thickness of the skin. In addition, the surface of probe 102 optionally has dimensions which are not substantially greater than the thickness of the internal tissue of body portion 120. In an exemplary embodiment of the invention, the length of probe 102 is not greater than twice the depth of the internal tissue. The use of a probe 102 that adheres to these limitations allows for ignoring the thickness of the skin and/or of the internal tissue, in calculating the internal tissue resistance.

In some embodiments of the invention, the applied electrical stimulus signals have relatively low frequencies $\omega$, at which the total impedance of the body tissue is much smaller than the impedance of the skin, i.e., $|1/r_b + i\omega C_b| \gg |1/r_s + i\omega C_s|$ where $r_b$, $r_s$ are the real impedance of the body and skin respectively, and $C_b$, $C_s$ are the capacitance of the body and skin, respectively. Alternatively or additionally, the frequencies used are relatively low, such that the capacitance of the body tissue may be neglected and/or the reactive impedance component of the skin is low relative to its real impedance component. In some embodiments of the invention, the frequencies used are up to about 5-8 kHz. Use of relatively low frequencies is sometimes better suited for differentiation between healthy and malignant anomalies. Alternatively or additionally, higher frequencies, i.e., in the 5-30 kHz region, are used.

It is noted that the resultant equations may be used advantageously also in some cases in which the simplifications do not strictly hold. Alternatively or additionally, equations without one or more of the above simplifications may be used in the method of FIG. 5. In this alternative, the fitting of the generated maps into the equations are optionally performed using a larger number of generated maps. Furthermore, other (e.g., more complex) models, which take into account additional factors of the body portion, such as the skin thickness, the breast width, and/or different internal tissue impedance values for different regions, are used. Optionally, iterative non-linear optimization methods are used in performing the fitting into the more complex models.

Returning to FIG. 4, in some embodiments of the invention, before or after calculating (412) the malignancy score, processor 110 evaluates the calculation of the tissue resistance $r_b$ in order to determine (414) a reliability of the calculated malignancy score. Optionally, if the evaluation of the calculations indicates a low reliability, additional calculations and/or a repeated measuring session are performed. Alternatively, the malignancy score is raised by a predetermined amount, responsive to the low reliability, so as to indicate the need for additional tests whenever there is a doubt.

In some embodiments of the invention, the evaluation of the calculations comprises relating to the fitting error when values are fit into equations (1) and/or (2). Alternatively or additionally, the reliability evaluation depends on a comparison of the skin impedance values to expected values. In some embodiments of the invention in which matrix $F_b$ is determined best on fitting a plurality of maps into equation (2), the reliability evaluation includes comparing the resultant matrix $F_b$ to predetermined models thereof. If the resultant matrix $F_b$ is similar to an expected model, the resultant value of resistance matrix $\bar{r}_b$ is optionally considered highly reliable. If, however, the resultant matrix $F_b$ is different from an expected model, the resultant value of resistance matrix $\bar{r}_b$ is considered having low reliability.

Alternatively or additionally to determining (410) a body tissue resistance $r_b$, in some embodiments of the invention, the generated maps $M_f$ and/or the distorted resistance matrix $\tilde{r}_b$ are compared to predetermined representative maps of healthy and/or non-healthy tissue. Optionally, clinical tests are performed on a plurality of patients which have healthy tissue and on a plurality of patients with tissue including various types of tumors. According to the results of the clinical tests the predetermined representative maps are generated. Alternatively or additionally, the representative maps are generated according to a theoretical analysis of the impedance of healthy and/or non-healthy tissue. For example, for uniform tissue, lower measured impedance values (due to increased current) are expected at the edges of surface probe 102, than for internal elements of the probe. Conversely, if a tumor is located beneath the center of surface probe 102, lower impedance values are expected in the center elements of surface probe 102.

Although in the above description the plurality of maps $M_f$ were generated using stimulus signals of different frequencies, in some embodiments of the invention, the plurality of maps are generated responsive to stimulus signals with additional and/or other differences, which affect the impedance of the skin and/or internal body tissue. For example, different maps may be generated for stimulus signals applied from different locations and/or in different patterns, such as described in the above referenced WO 01/43630. Alternatively or additionally, different maps may be generated for different levels of pressure applied to the breast.

In some embodiments of the invention, the malignancy score is determined based on measurements from a plurality of locations on the breast. Optionally, surface probe 102 is placed on a plurality of surface locations and in each location a location resistance $r_b$ of the internal tissue beneath the surface location is determined. The malignancy score is then determined as a function of the determined location resistance $r_b$ values. Alternatively or additionally, for each location, a location malignancy score is determined and the malignancy score is determined as a function of the location malignancy scores.

Alternatively or additionally to placing the surface probe 102 on a plurality of locations, a large probe (e.g., 60×45 elements) is used, and different element groups of the probe participate in the mapping at different stages. Thus, the "placement" of the effective probe may be performed accurately and more simply.

Alternatively to sensing the signals by sensing elements 106 while substantially all the elements 106 are held at an equipotential, in some embodiments of the invention the sensing is performed while substantially all the elements 106 are floating electrically. Optionally, in generating (406) the impedance maps, each of sensing elements 106 is sequentially connected to scanner device 58. While the current in each sensing element 106 is being measured, the remaining elements are kept floating. In this alternative, the geometrical matrix $F_b$ is optionally taken as the unit matrix I, as the measurements of the different sensing elements 106 are generally not related to their position on surface probe 102.

In some embodiments of the invention, a plurality of maps including measurements from different subsets of elements, are acquired based on a single stimulus signal. Optionally, the elements 106 not participating in the acquisition are kept floating. In some embodiments of the invention, an acquisition process includes generation of a plurality of maps with overlapping, increasing areas. Optionally, a first map includes a single, first, pixel, a second map includes the first pixel together with its eight neighbors, a third map includes the pixels from the second map and their surrounding neighbors, etc. Thus, a plurality of maps with increasing overlapping areas are produced. Each map is optionally processed using the method described above, including the use of a respective matrix $F_b$ for each map. The overlapping maps may be used to receive more information on the cupping effect of the tissue in addition to, or instead of, maps from different frequencies. In some embodiments of the invention, the effective width of the breast is determined according to the maps, e.g., by finding the largest map which still shows a cupping effect. Alternatively or additionally, a series of overlapping maps is generated, and the largest map with a cupping effect is used in the calculations.

Alternatively or additionally, a map acquired for an inclusive group of pixels, which may include all the pixels or fewer than all the pixels, is analyzed for different subsets thereof.

Alternatively or additionally to mapping the body tissue resistance $r_b$, processor 110 determines the capacitance of the internal body tissue and uses the capacitance as an indicator of whether the tissue beneath probe 102 is healthy. Optionally, the capacitance is determined using high frequency stimulus signals, for example between 0.1-2 MHz. Further alternatively or additionally, processor 110 determines the real and/or imaginary impedance of the skin on which surface probe 102 is placed. The determined impedance may be used, for example, as a skin cancer indicator. Alternatively or additionally, the skin admittance is used as an indicator of whether an anomaly is located within the body tissue beneath the skin. In some cases, irregular admittance values of the skin are indicative of unhealthy internal tissue.

The above described methods are not limited to use in determining the impedance of internal tissue beneath a layer of skin. Rather, these methods may be used advantageously for separating desired impedance values from other values which are not of interest or are required for separate analysis. In an exemplary embodiment of the invention, any of these methods is used to determine the impedance of tissue beneath other masking layers, for example under capacitive contact layers, as is now described.

Although the above description relates to generating a malignancy score for a breast, the above methods, particularly those of FIGS. 4 and 5, and/or the use of the indicator frequency, may be used for body areas other than the breast. In addition, these methods may be used for procedures other than generating a malignancy score, such as for other breast scanning procedures, for detecting suspicious tumors, for procedures directed to locating anomalies and/or for identifying whether an anomaly is malignant. For example, an examination procedure optionally includes determining the tissue impedance $r_b$ at different surface locations of an examined body portion. The tissue impedance $r_b$ of different areas are optionally compared in order to find areas which have suspiciously high and/or low values. In an exemplary embodiment of the invention, the resistance of a breast is mapped by placing surface probe 102 at 9 points around the breast and determining resistance $r_b$ for each point.

It will be appreciated that the above-described methods may be varied in many ways, including, changing the order of steps, and/or performing a plurality of steps concurrently. For example, surface probe 102 is not limited to any specific shape. In some embodiments of the invention, surface probe 102 may have a circular shape, so as to minimize the extent of the perimeter of the probe relative to its surface area. Alternatively, surface probe 102 has a polygon shape, triangular shape and/or a rectangular shape. It should also be appreciated that the above described description of methods and apparatus are to be interpreted as including apparatus for carrying out the methods, and methods of using the apparatus.

The present invention has been described using non-limiting detailed descriptions of embodiments thereof that are provided by way of example and are not intended to limit the scope of the invention. It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art. Furthermore, the terms "comprise," "include," "have" and their conjugates, shall mean, when used in the claims, "including but not necessarily limited to."

It is noted that some of the above described embodiments may describe the best mode contemplated by the inventors and therefore may include structure, acts or details of structures and acts that may not be essential to the invention and which are described as examples. Structure and acts described herein are replaceable by equivalents which perform the same function, even if the structure or acts are different, as known in the art. Therefore, the scope of the invention is limited only by the elements and limitations as used in the claims.

The invention claimed is:

1. Apparatus for breast examination, comprising:
   a sensing unit including a multi-element probe comprising a plurality of sensing elements capable of sensing electrical signals from a surface of a breast, including at least a portion of the nipple thereof;
   a processor operative to acquire electrical signals from each of a plurality of points on the nipple of the breast through a plurality of respective sensing elements of the sensing unit, to determine dielectric values corresponding to a plurality of points on the nipple, responsive to the acquired electrical signals and to generate based on the dielectric values corresponding to the plurality of points on the nipple, a malignancy score relating to the need of additional testing of the breast; and
   a display operative to indicate at least the range of the malignancy score.

2. Apparatus according to claim 1, wherein the processor is operative to determine the malignancy score as a function of an electrical parameter of the breast.

3. Apparatus according to claim 2, wherein the electrical parameter comprises an electrical parameter determined directly from the sensed signals.

4. Apparatus according to claim 2, wherein the electrical parameter comprises an electrical parameter of inner tissue of the breast.

5. Apparatus according to claim 2, wherein the processor is adapted to determine the malignancy score as a binary function of the electrical parameter of the breast.

6. Apparatus according to claim 1, wherein the malignancy score comprises a binary malignancy score.

7. Apparatus according to claim 1, wherein the processor is adapted to generate an impedance based image including a plurality of pixels corresponding to the nipple of the breast and wherein the malignancy score is determined responsive to the image.

8. Apparatus according to claim 7, wherein the processor is adapted to generate the malignancy score responsive to an impedance image corresponding to the areola.

9. Apparatus according to claim 1, wherein the malignancy score is operative to indicate a need for additional tests on the average for more than twice the percentage in the population of malignant breasts.

10. Apparatus according to claim 9, wherein the malignancy score is adapted to indicate a need for additional tests on the average for more than ten times the percentage in the population of malignant breasts.

11. Apparatus according to claim 10, wherein the malignancy score is adapted to indicate a need for additional tests on the average for about 5% or more of the examined patients.

12. Apparatus according to claim 1 wherein the processor is operative to delineate areas of the nipple and areas outside the nipple, responsive to values of the sensed electrical signals.

13. Apparatus according to claim 1 wherein the probe comprises a hole or depression suitable for fitting the tip of the nipple therein.

14. Apparatus according to claim 13 wherein an outer periphery of the probe is within 1 cm of the center of the hole or depression.

15. Apparatus according to claim 13 wherein an outer periphery of the probe is within 1.5 cm of the center of the hole or depression.

16. Apparatus according to claim 13 and including a plurality of different probes, adapted for matching different sized nipples.

17. Apparatus according to claim 1 wherein an outer periphery of the probe is within an outer edge of the nipple.

18. Apparatus according to claim 1 wherein the probe comprises an outer guard ring and an inner sensing electrode.

19. Apparatus according to claim 1 wherein the probe comprises a single sensing electrode having an outer dimension of less than 1 cm.

20. Apparatus according to claim 1, wherein the probe comprises a marking of a position to be placed on the nipple.

21. Apparatus according to claim 1, wherein the sensing unit comprises at least one sensing element adapted to be placed on a surface of the body other than the breast.

22. Apparatus according to claim 21 wherein the processor utilizes signals from said sensing element to adjust the values of said signals from the breast portion utilized in determining said score.

23. Apparatus according to claim 1, wherein the processor is calibrated to give a score for young women up to about age 45.

24. Apparatus according to claim 1, wherein the processor is adapted to acquire the electrical signals from the plurality of points concurrently.

25. Apparatus for breast examination, comprising:
a sensing unit capable of sensing electrical signals from a breast, including at least a portion of the nipple thereof, through a plurality of sensing elements;
a processor adapted to determine which of the sensing elements acquired signals from the nipple portion at least partially responsive to values of the sensed signals from the sensing elements and to generate, responsive to sensed signals from the sensing elements determined to acquire signals from the nipple portion, a malignancy score relating to the need of additional testing of the breast; and
a human output interface adapted to provide the malignancy score to a user.

26. Apparatus according to claim 25 wherein the sensing unit comprises a surface probe.

27. Apparatus according to claim 26, wherein the surface probe comprises a multi-element probe.

28. Apparatus according to claim 26, wherein the surface probe comprises a marking of a position to be placed on the nipple.

29. Apparatus according to claim 26, wherein the surface probe comprises a hole or depression adapted to receive the nipple.

30. Apparatus according to claim 26, wherein the surface probe comprises at least one sensing element adapted to be placed on a surface remote from the nipple.

31. Apparatus according to claim 30, wherein the processor utilizes signals from said sensing element to adjust the values of said signals from the nipple portion utilized in determining said score.

32. Apparatus according to claim 25, wherein the score is a binary score.

33. Apparatus according to claim 25, wherein the processor is calibrated to give a score for young women up to about age 45.

34. Apparatus according to claim 25, wherein the plurality of sensing elements comprise at least one sensing element adapted to be placed on a surface remote from the breast.

35. A method of breast examination, comprising:
sensing electrical signals from a surface of a breast, including from each of a plurality of points on at least a portion of the nipple thereof;
determining dielectric parameter values corresponding to a plurality of points on the nipple, responsive to the sensed electrical signals;
analyzing the sensed electrical signals so as to generate a malignancy score relating to the need of additional testing of the breast, responsive to the determined dielectric parameter values corresponding to the plurality of points; and
displaying at least a range of the malignancy score.

36. A method according to claim 35, wherein the malignancy score is determined from a nipple portion of the image.

37. A method according to claim 35, wherein the analyzing comprises delineating areas of the nipple in the image.

38. A method according to claim 35, comprising providing electrical signals to the patient and wherein sensing the electrical signals comprises sensing responsive to the provided electrical signals.

39. A method according to claim 35, wherein determining the dielectric parameter values comprises generating an impedance image including at least a nipple portion.

* * * * *